(12) United States Patent
Babu et al.

(10) Patent No.: US 7,514,410 B2
(45) Date of Patent: Apr. 7, 2009

(54) HEPATITIS C THERAPIES

(75) Inventors: Yarlagadda S. Babu, Birmingham, AL (US); Pooran Chand, Birmingham, AL (US); Minwan Wu, Vestavia Hills, AL (US); Pravin L. Kotian, Hoover, AL (US); V. Satish Kumar, Birmingham, AL (US); Tsu-Hsing Lin, Vestavia Hills, AL (US); Yahya El-Kattan, Vestavia Hills, AL (US); Ajit K. Ghosh, Birmingham, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 351 days.

(21) Appl. No.: 11/388,060

(22) Filed: Mar. 23, 2006

(65) Prior Publication Data

US 2006/0234963 A1    Oct. 19, 2006

Related U.S. Application Data

(60) Provisional application No. 60/665,832, filed on Mar. 29, 2005, provisional application No. 60/692,572, filed on Jun. 22, 2005.

(51) Int. Cl.
*A01N 43/04* (2006.01)
(52) U.S. Cl. .................................... 514/23; 536/29.2
(58) Field of Classification Search .................. None
See application file for complete search history.

(56) References Cited

U.S. PATENT DOCUMENTS

| 4,584,369 | A  | 4/1986 | Klein et al. |
| 6,339,089 | B2 | 1/2002 | Nakashima et al. |
| 2006/0165655 | A1 | 7/2006 | Babu et al. |

FOREIGN PATENT DOCUMENTS

| EP | 0 071 227 | 2/1983 |
| WO | WO 97/29110 | 8/1997 |
| WO | WO 98/08847 | 3/1998 |
| WO | WO 98/49899 | 11/1998 |
| WO | WO 03/051899 | 6/2003 |
| WO | WO 2005/123087 | 12/2005 |
| WO | WO 2006/050161 | 5/2006 |

OTHER PUBLICATIONS

Leyssen et al. Clinical Microbiology Reviews (2000), pp. 67-82.*

Alexander et al., "(Acyloxy)alkyl carbamates as novel bioreversible prodrugs for amines: Increased permeation through biological membranes", *J Med Chem*, 31(2), 318-322 (1988).
Blight et al., "Efficient initiation of HCV RNA replication in cell culture", *Science*, 290, 1972-1974 (2000).
Bodor, "Soft drugs. 1. Labile quaternary ammonium salts as soft antimicrobials", *J Med Chem*, 23(5), 469-474 (1980).
Bruenn, "Relationships among the positive strand and double-strand RNA viruses as viewed through their RNA-dependent RNA polymerases", *Nucleic Acids Res*, 19(2), 217-226 (1991).
Davis, "Current therapy for chronic hepatitis C", *Gastroenterology*, 118, S104-S114 (2000).
Hirota et al., "Discovery of 8-hydroxyadenines as a novel type as interferon inducer", *J Med Chem*, 45(25), 5419-5422 (2002).
Korba et al., "Use of a standardized cell culture assay to assess activities of nucleoside analogs against hepatitis B virus replication", *Aniviral Res. 19*(1), 55-70 (1992).
Kurimoto et al., "Synthesis and structure-activity relationships of 2-amino-8-hydroxyadenines as orally active interferon inducing agents", *Bioorg Med Chem*, 11(24), 5501-5508 (2003).
Lefebvre et al., "Mononucleoside phosphotriester derivatives with S-acyl-2-thioethyl bioreversible phosphate-protecting groups: Intracellular delivery of 3'-azido-2',3'-dideoxythymidine 5'-monophosphate", *J Med Chem*, 38(20), 3941-3950 (1995).
Okuse et al., "Enhancement of antiviral activity against hepatitis C virus in vitro by interferon combination therapy", *Antiviral Res*, 65(1), 23-34 (2005).
International Search Report for International Application No. PCT/US2006/010948, mailed Sep. 7, 2006.
Bhattacharya et al., "Studies on the Synthesis of Furo [3,2-d] Pyrimidine C-Nucleosides: New Inosine Analogues with Antiprotozoan Activity", *Nucleosides & Nucleotides*, 9(8), 1021-1043 (1990).
Bhattacharya et al., "Synthesis of Furo[3,2-d] Pyrimidine Nucleosides: A Novel C-Nucleoside Isostere of Adenosine", *Tetrahedron Letters*, 27(7), 815-818 (1986).
Ikegami et al, "Structure of Pyrrolosine: A Novel Inhibitor of RNA Synthesis, from the Actinomycete *Streptomyces albus*", *J. Am. Chem. Soc.*, 112, 9668-9669 (1990).
Jourdan et al., "Synthesis of Thieno[3,2-d] pyrimidine-2,4-diones Cyclic and Acyclic Nucleosides as Potential Anti HIV Agents", *J. Heterocyclic Chem.*, 31, 305-312 (1994).
Morris et al., "New Synthesis of 7-Substituted-2-aminothieno- and Furo[3,2-d] pyrimidines", *J. Heterocyclic Chem.*, 36, 423-427 (1999).
Otter et al., "A Corrected Structure for Pyrrolosine", *J. Am. Chem. Soc.*, 114, 668-671 (1992).

* cited by examiner

*Primary Examiner*—Patrick T Lewis
(74) *Attorney, Agent, or Firm*—Viksnins Harris & Padys PLLP

(57) ABSTRACT

The invention provides methods for treating hepatitis C viral infections and related viral infections, as well as compounds and compositions that are useful for treating such infections.

42 Claims, No Drawings

HEPATITIS C THERAPIES

RELATED APPLICATIONS

This application claims priority to International Application No. PCT/US2005/039072 filed Oct. 28, 2005; and this application also claims the benefit of priority of U.S. Provisional Application No. 60/665,832, filed Mar. 29, 2005 and the benefit of priority of U.S. Provisional Application No. 60/692,572, filed Jun. 22, 2005; these applications are incorporated herein by reference in their entirety.

BACKGROUND OF THE INVENTION

Viral diseases are a major cause of death and economic loss in the world. The Flaviviridae family of viruses consists of three genera: the flaviviruses (including dengue, West Nile, and yellow fever viruses), hepacivirus (HCV), and the pestiviruses (including bovine viral diarrhea virus, BVDV). The disease states and conditions caused by members of this family include yellow fever, dengue, Japanese encephalitis, St. Louis encephalitis, Hepatitis B and C, West Nile disease, and AIDS. Currently, human immunodeficiency virus (HIV), hepatitis B virus (HBV) and hepatitis C virus (HCV) infections are responsible for the largest number of viral related deaths worldwide. Although there are some drugs useful for treating HIV, there are only a few drugs useful for treating HBV, and no drugs that are broadly useful for treating HCV.

Ribavirin (1-β-D-ribofuranosyl-1-1,2,4-triazole-3-carboxamide) is a synthetic, non-interferon-inducing, broad spectrum antiviral nucleoside. Ribavirin is structurally similar to guanosine, and has in vitro activity against several DNA and RNA viruses including Flaviviridae (Davis. Gastroenterology 118:S104-S114, 2000). Ribavirin reduces serum amino transferase levels to normal in 40% of patients, but it does not lower serum levels of HCV-RNA (Davis. Gastroenterology 118:S104-S114, 2000). Thus, ribavirin alone is not effective in reducing viral RNA levels. Additionally, ribavirin has significant toxicity and is known to induce anemia.

Interferons (IFNs) are compounds which have been commercially available for the treatment of chronic hepatitis for nearly a decade. IFNs are glycoproteins produced by immune cells in response to viral infection. IFNs inhibit viral replication of many viruses, including HCV. When used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Davis. Gastroenterology 118:S104-S114, 2000).

HCV is a positive single stranded RNA virus with a well characterized RNA-dependent RNA polymerase (RdRp) and a well characterized disease progression. HCV has infected an estimated 170 million people worldwide, leading to a major health crisis as a result of the disease. Indeed, during the next few years the number of deaths from HCV-related liver disease and hepatocellular carcinoma may overtake those caused by AIDS. Egypt is the hardest hit country in the world, with 23% of the population estimated to be carrying the virus; whereas, in the USA the prevalence of chronic infections has recently been determined to be around 1.87% (2.7 million persons). HCV infections become chronic in about 50% of cases. Of these, about 20% develop liver cirrhosis that can lead to liver failure, including hepatocellular carcinoma.

The NS5B region of HCV encodes a 65 KDa RdRp thought to be responsible for viral genome replication. RdRps function as the catalytic subunit of the viral replicase required for the replication of all positive-strand viruses. The NS5B protein has been well characterized, shown to possess the conserved GDD motif of RdRps and in vitro assay systems have been reported. Cellular localization studies revealed that NS5B is membrane-associated in the endoplasmic reticulum like NS5A, suggesting that those two proteins may remain associated with one another after proteolytic processing. Additional evidence suggests that NS3, NS4A and NS5B interact with each other to form a complex that functions as part of the replication machinery of HCV.

The X-ray crystal structure of NS5B apoenzyme has been determined and three very recent publications describe the unusual shape of the molecule. This unique shape for a polymerase, resembling a flat sphere, is attributed to extensive interactions between the fingers and thumb subdomains in such a way that the active site is completely encircled, forming a cavity 15 Å across and 20 Å deep. Modeling studies showed that the NS5B apoenzyme can accommodate the template-primer without large movement of the subdomains, suggesting that the structure is preserved during the polymerization reaction. The RdRp polypeptides from various members of the Flaviviridae family and other viral families have been shown to be conserved (J. A. Bruenn, Nucleic Acids Research, Vol. 19, No. 2 p. 217, 1991).

Viral diseases are one of the major causes of deaths and economic losses in the world. Out of various viral diseases, HIV, HBV and HCV infections are more important and responsible for a large number of deaths. There are some drugs for HIV, only a few for HBV but no good drug for HCV. Hepatitis C is a viral liver disease, caused by infection with the hepatitis C virus (HCV). There are approximately 170 million people worldwide with chronic HCV infection, of which about 2.7 million are in the United States. HCV is a leading cause of cirrhosis, a common cause of hepatocellular carcinoma, and is the leading cause of liver transplantation in the United States. Currently, α-interferon monotherapy and α-interferon-ribavirin combination therapy are the only approved treatments for HCV.

U.S. Pat. No. 4,584,369 is directed to certain compounds that are reported to inhibit the growth of leukemia cells. In the Background section of the patent it states that some beta-glycosyl C-Nucleoside compounds appear to have some antiviral activity. There is no antiviral data reported in the patent for any compounds and there is no disclosure regarding which viruses the beta-glycosyl C-Nucleoside compounds may have activity against.

SUMMARY OF THE INVENTION

It has been found that certain compounds inhibit a viral polymerase from the Flaviviridae family of viruses, HCV viral polymerase. Accordingly, the invention relates to certain fused furan, thiophene and pyrrole compounds and particularly to fused furan, thiophene and pyrrole compounds that are useful as inhibitors of hepatitis B, hepatitis C, Polio, Coxsackie A and B, Rhino, Echo, small pox, Ebola, and West Nile virus polymerases.

In one embodiment the invention provides a method for treating a viral infection selected from hepatitis B, hepatitis C, Polio, Coxsackie A and B, Rhino, Echo, small pox, Ebola, and West Nile in an animal (e.g. a human), comprising administering to the animal an effective amount of a compound of formula I:

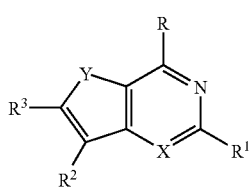

(I)

wherein:

X=N or CH;

Y=O, S or N—$R^4$;

R is $OR_3$, $SR_3$, $NR_3R_4$, $NR_3NR_4R_5$, alkyl, substituted alkyl, alkenyl, substituted alkenyl, alkynyl, substituted alkynyl, aryl, substituted aryl, $(CH_2)_nNR_aR_b$, $(CH_2)_nOR_a$, $C(=NR_a)NR_bR_c$, $(CH_2)_n$—$CH(NHR_3)CO_2R_4$, $(CH_2)_n$—S-alkyl, $(CH_2)_n$—S-aryl, Cl, F, Br, I, CN, $COOR_3$, $CONR_3R_4$, $NHC(=NR_3)NHR_4$, $NR_3OR_4$, $NR_3NO$, $NHCONHR_3$, $NR_3N=NR_4$, $NR_3N=CHR_4$, $NR_3C(O)NR_4R_5$, $NR_3C(S)NR_4R_5$, $NR_3C(O)OR_4$, CH=N—$OR_3$, $NR_3C(=NH)NR_4R_5$, $NR_3C(O)NR_4NR_5R_6$, O—$C(O)R_3$, OC(O)—$OR_3$, ONH—C(O)O-alkyl, ONHC(O)O-aryl, $ONR_3R_4$, $SNR_3R_4$, S—$ONR_3R_4$, or $SO_2NR_3R_4$;

n is 0, 1, 2, 3, 4, or 5;

$R^1$ is H, $NR_3R_4$, Cl, F, $OR_3$, $SR_3$, $NHCOR_3$, $NHSO_2R_3$, $NHCONHR_3$, CN, alkyl, aryl, $ONR_3R_4$, or $NR_3C(O)OR_4$;

$R^2$ is ribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose;

$R^3$ is H, alkyl, aryl, F, Cl, CN, $CO_2H$ or $NH_2$; and $R^4$ is H, OH, alkyl, aryl, —COO-alkyl, $CONH_2$, CONH-alkyl, O—C(O)-alkyl, O—C(O)-aryl or alkoxy;

$R_3$, $R_4$, $R_5$, and $R_6$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl OH, —COO-alkyl, $CONH_2$, CONH-alkyl, O—C(O)-alkyl, O—C(O)-aryl alkoxy and NO; or $R_3$ and $R_4$ together with the nitrogen to which they are attached form a pyrrolidino, piperidino, piperazino, azetidino, morpholino, pyrrolino, or thiomorpholino ring; or $R_4$ and $R_5$ together with the nitrogen to which they are attached form a pyrrolidino, piperidino, piperazino, azetidino, morpholino, pyrrolino, or thiomorpholino ring; wherein any ring formed by $R_3$ and $R_4$ or $R_4$ and $R_5$ is optionally substituted with one or more hydroxyl, halo, alkyl, substituted alkyl, alkenyl, substituted alkenyl, alkynyl, or substituted alkynyl; and $R_a$, $R_b$, and $R_c$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

or a pharmaceutically acceptable salt or prodrug thereof.

Certain compounds of formula I are novel. Accordingly, the invention also provides novel compounds of formula I as described herein as well as pharmaceutically acceptable salts and prodrugs thereof. For example, in one embodiment, the invention provides a compound of the formula:

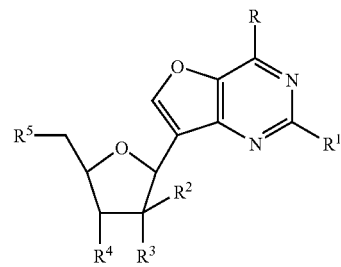

wherein:

R is $OR_a$, $SR_a$, $N_cR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)$ $NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, CH=N—$OR_a$, $NR_aC(=NH)NR_bR_c$, $NR_aC(O)NR_bNR_cR_d$, O—$C(O)R_a$, OC(O)—$OR_a$, ONH—C(O)O-alkyl, ONHC(O)O-aryl, $ONR_aR_b$, $SNR_aR_b$, S—$ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, and $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

or a pharmaceutically acceptable salt or prodrug thereof.

In another embodiment the invention provides a method for inhibiting an HCV RNA or DNA polymerase comprising contacting the polymerase in vitro or in vivo with an effective inhibitory amount of a compound of formula I or a pharmaceutically acceptable salt or prodrug thereof.

In another embodiment the invention provides a pharmaceutical composition comprising a compound of formula I or a pharmaceutically acceptable salt or prodrug thereof; and a pharmaceutically acceptable carrier. The composition can optionally comprise one or more additional anti-viral agents, immune modulators, or interferon inducers.

In another embodiment the invention provides a method for treating hepatitis C in an animal comprising administering to the animal an effective amount of a compound of formula I, or a pharmaceutically acceptable salt or prodrug thereof.

In another embodiment the invention provides a method for inhibiting an HCV RNA or DNA polymerase comprising contacting the polymerase (in vitro or in vivo) with an effective inhibitory amount of a compound of formula I, or a pharmaceutically acceptable salt or prodrug thereof.

DETAILED DESCRIPTION OF THE INVENTION

Definitions

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

The terms "treat", "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

The term "animal" as used herein refers to any animal, including mammals, such as, but not limited to, mice, rats, other rodents, rabbits, dogs, cats, swine, cattle, sheep, horses, and primates. In one specific embodiment of the invention the animal is a human.

The term "therapeutically effective amount", in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The term "alkyl" as used herein refers to alkyl groups having from 1 to 6 carbon atoms. This term is exemplified by groups such as methyl, ethyl, n-propyl, iso-propyl, n-butyl, t-butyl, n-pentyl and the like. In a specific embodiment, the alkyl groups have from 1-4 carbon atoms and are referred to as lower alkyl.

The terms "alkenyl" or "alkene" as used herein refers to an alkenyl group having from 2 to 10 carbon atoms and having at least 1 site of alkenyl unsaturation. Such groups are exemplified by vinyl(ethen-1-yl), allyl, but-3-en-1-yl, and the like.

The term "alkynyl" or "alkyne" as used herein refers to an alkynyl group having from 2-10 carbon atoms and having at least 1 site of alkynyl unsaturation. Such groups are exemplified by, but not limited to, ethyn-1-yl, propyn-1-yl, propyn-2-yl, 1-methylprop-2-yn-1-yl, butyn-1-yl, butyn-2-yl, butyn-3-yl, and the like.

The term "alkoxy" refers to the group alkyl-O—.

The term "acyl" as used herein refers to the groups alkyl-C(O)—, alkenyl-C(O)—, alkynyl-C(O)—, cycloalkyl-C(O)—, aryl-C(O)—, heteroaryl-C(O)—, and heterocyclic-C(O).

The term "acylamino" as used herein refers to the group-C(O)NZ$_1$Z$_2$ where each Z$_1$ and Z$_2$ are independently selected from the group consisting of hydrogen, alkyl, alkenyl, and alkynyl.

The term "acyloxy" as used herein refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

The term "oxyacyl" as used herein refers to the groups alkyl-OC(O)—, alkenyl-OC(O)—, alkynyl-OC(O)—, aryl-OC(O)—, cycloalkyl-OC(O)—, heteroaryl-OC(O)—, and heterocyclic-OC(O)—.

The term "amino" as used herein refers to the group —NH$_2$.

The term "substituted amino" as used herein refers to the group —NZ$_1$Z$_2$ where Z$_1$ and Z$_2$ are as described above in the definition of acylamino, provided that Z$_1$ and Z$_2$ are both not hydrogen.

The term "aminoacyl" as used herein refers to the groups —NZ$_3$C(O)alkyl, —NZ$_3$C(O)cycloalkyl, —NZ$_3$C(O)alkenyl, —NZ$_3$C(O)alkynyl, —NZ$_3$C(O)aryl, —NZ$_3$C(O)heteroaryl, and —NZ$_3$C(O)heterocyclic, where Z$_3$ is hydrogen or alkyl.

The term "aryl" as used herein refers to a monovalent aromatic cyclic group of from 6 to 14 carbon atoms having a single ring (e.g., phenyl) or multiple condensed rings (e.g., naphthyl or anthryl) which condensed rings may or may not be aromatic. Exemplary aryls include, but are not limited to, phenyl and naphthyl.

The term "aryloxy" as used herein refers to the group aryl-O— that includes, by way of example but not limitation, phenoxy, naphthoxy, and the like.

The term "carboxyl" as used herein refers to —COOH or salts thereof.

The term "carboxyl esters" as used herein refers to the groups-C(O)O-alkyl, and —C(O)O-aryl.

The term "cycloalkyl" as used herein refers to a saturated or unsaturated cyclic hydrocarbon ring systems, such as those containing 1 to 3 rings and 3 to 7 carbons per ring. Exemplary groups include but are not limited to cyclopropyl, cyclobutyl, cyclopentyl, cyclohexyl, cycloheptyl, and adamantyl.

The term "cycloalkoxy" as used herein refers to —O-cycloalkyl groups.

The term "formyl" as used herein refers to HC(O)—.

The term "halogen" as used herein refers to fluoro, chloro, bromo and iodo.

The term "heteroaryl" as used herein refers to an aromatic group of from 5 to 10 carbon atoms and 1 to 4 heteroatoms selected from the group consisting of oxygen, nitrogen, sulfur in the ring. The sulfur and nitrogen heteroatoms atoms may also be present in their oxidized forms. Such heteroaryl groups can have a single ring (e.g., pyridyl or furyl) or multiple condensed rings (e.g., indolizinyl or benzothienyl) wherein the condensed rings may or may not be aromatic and/or contain a heteroatom. Exemplary heteroaryl groups include, but are not limited to, heteroaryls include pyridyl, pyrrolyl, thienyl, indolyl, thiophenyl, and furyl.

The term "heteroaryloxy" as used herein refers to the group —O-heteroaryl.

The term "heterocycle" or "heterocyclic" refers to a saturated or unsaturated group (but not heteroaryl) having a single ring or multiple condensed rings, from 3 to 10 carbon atoms and from 1 to 4 hetero atoms selected from the group consisting of nitrogen, oxygen, sulfur, within the ring wherein, in fused ring systems, one or more the rings can be cycloalkyl, aryl or heteroaryl provided that the point of attachment is through the heterocyclic ring. The sulfur and nitrogen atoms may also be present in their oxidized forms.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "phosphate" as used herein refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood that the initial oxygen of the mono-, di-, and triphosphate may include the oxygen atom of a sugar.

The term "phosphate esters" as used herein refers to the mono-, di-and tri-phosphate groups described above wherein one or more of the hydroxyl groups is replaced by an alkoxy group.

The term "substituted alkyl" as used herein refers to an alkyl group having from 1 to 3 substituents, said substituents being selected from the group consisting of alkoxy, substituted alkoxy, acyl, substituted acyl, acylamino, acyloxy, oxyacyl, amino, substituted amino, aminoacyl, aryl, substituted aryl, aryloxy, substituted aryloxy, cyano, halogen, hydroxyl, nitro, N$_3$, carboxyl, carboxyl esters, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, heteroaryl, substituted heteroaryl, heterocyclic, and substituted heterocyclic.

The term "substituted alkenyl" as used herein refers to alkenyl groups having from 1 to 3 substituents, said substituents being selected from those describe above for a substituted alkyl.

The term "substituted alkynyl" as used herein refers to alkynyl groups having from 1 to 3 substituents, said substituents being selected those describe above for a substituted alkyl.

The term "substituted alkoxy" as used herein refers to the group substituted alkyl-O—.

The term "substituted acyl" as used herein refers to the groups substituted alkyl-C(O)—, substituted alkenyl-C(O)—, substituted alkynyl-C(O)—, substituted cycloalkyl-C(O)—, substituted aryl-C(O)—, substituted heteroaryl-C(O), and substituted heterocyclic-C(O)—.

The term "substituted aryl" as used herein refers to aryl groups which are substituted with from 1 to 3 substituents selected from alkyl, substituted alkyl, alkenyl, substituted alkenyl, alkynyl and substituted alkynyl, and those substituents described above in the definition of substituted alkyl.

The term "substituted aryloxy" as used herein refers to substituted aryl-O-groups.

The term "substituted cycloalkyl" as used herein refers to a cycloalkyl having from 1 to 5 substituents selected from the group consisting of oxo (═O), thioxo (═S), alkyl, substituted alkyl, and those substituents described in the definition of substituted alkyl.

The term "substituted cycloalkoxy" as used herein refers to —O-substituted cycloalkyl groups.

The term "substituted heteroaryl" as used herein refers to heteroaryl groups that are substituted with from 1 to 3 substituents selected from the same group of substituents defined for substituted aryl.

The term "substituted heteroaryloxy" as used herein refers to the group —O-substituted heteroaryl.

The term "substituted heterocycle" or "substituted heterocyclic" or "substituted heterocycloalkyl" refers to heterocycle groups that are substituted with from 1 to 3 of the same substituents as defined for substituted aryl.

The term "thiol" as used herein refers to the group —SH.

The term "thioalkyl" or "alkylthioether" or "thioalkoxy" refers to the group-S-alkyl.

The term "thiocycloalkyl" as used herein refers to the group —S-cycloalkyl.

The term "thioaryl" as used herein refers to the group —S-aryl.

The term "thioheteroaryl" as used herein refers to the group —S-heteroaryl.

The term "thioheterocyclic" as used herein refers to the group —S-heterocyclic.

The term "amino acid sidechain" refers to the $Z_7$ substituent of α-amino acids of the formula $Z_6NHCH(Z_7)COOH$ where $Z_7$ is selected from the group consisting of hydrogen, alkyl, and aryl and $Z_6$ is hydrogen or together with $Z_7$ and the nitrogen and carbon atoms bound thereto respectively form a heterocyclic ring. In one embodiment, the α-amino acid sidechain is the sidechain one of the twenty naturally occurring L amino acids.

Sugars described herein may either be in D or L configuration.

Specific values listed below for radicals, substituents, and ranges, are for illustration only; they do not exclude other defined values or other values within defined ranges for the radicals and substituents A specific value for R is OR$_a$, Cl, SR$_a$, NR$_e$R$_f$, aryl or NR$_a$NR$_b$R$_c$; wherein R$_a$, R$_b$, R$_c$, and R$_d$ are independently selected from the group consisting of H, alkyl, alkenyl, alkynyl, cycloalkyl, heterocyclic, aryl, acyl, SO$_2$-alkyl and NO; or R$_b$ and R$_c$ together with the nitrogen to which they are attached form a pyrrolidino, piperidino, piperazino, azetidino, morpholino, pyrrolino, or thiomorpholino ring; Re is alkyl, alkenyl, alkynyl, cycloalkyl, heterocyclic, aryl, acyl, SO$_2$-alkyl or NO; and R$_f$ is H, alkyl, alkenyl, alkynyl, cycloalkyl, heterocyclic, aryl, acyl, SO$_2$-alkyl and NO; or R$_e$ and R$_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl.

A specific value for R is hydroxy, chloro, methoxy, mercapto, methylthio, methylamino, isopropylamino, propylamino, ethylamino, dimethylamino, cyclopropylamino, 2-aminoethylamino, 1-(2-hydroxyethyl)hydrazino, hydrazino, 1-methylhydrazino, azetidino, pyrrolidino, imidazolylpropylamino, pyrrolino, morpholino, piperazino, hydroxyethylamino, bis-hydroxyethylamino, hydroxypropylamino, hydroxyethylpyrrolidino, or 1-methyl-2-hydroxyethylamino.

A specific value for $R^1$ is $NR_eR_f$.

A specific compound is 4-methylamino-7-β-(D-ribofuranosyl)-furo[3,2-d]pyrimidine; 4-Ethylamino-7-β-(D-ribofuranosyl)-furo[3,2-d]pyrimidine; 4-Isopropylamino-7-β-(D-ribofuranosyl)-furo[3,2-d]pyrimidine; 4-Dimethylamino-7-β-(D-ribofuranosyl)-furo[3,2-d]pyrimidine; 4-n-Propylamino-7-β-(D-ribofuranosyl)-furo[3,2-d]pyrimidine; 4-(N-3-pyrrolino)-7-β-(D-ribofuranosyl)-furo[3,2-d]pyrimidine; 4-(2-hydroxymethylpyrrolidino)-7-β-(D-ribofuranosyl)-furo[3,2-d]pyrimidine; 4-(3-N-imidazolyl-n-propylamino)-7-β-(D-ribofuranosyl)-furo[3,2-d]pyrimidine; 4-N-morpholino-7-β-(D-ribofuranosyl)-furo[3,2-d]pyrimidine; 4-N-piperazino-7-β-(D-ribofuranosyl)-furo[3,2-d]pyrimidine; 4-(hydroxyethylamino)-7-β-(D-ribofuranosyl)-furo[3,2-d]pyrimidine; 4-(N-bis-hydroxyethylamino)-7-β-(D-ribofuranosyl)-furo[3,2-d]pyrimidine; 4-(3-hydroxypropylamino)-7-β-(D-ribofuranosyl)-furo[3,2-d]pyrimidine; or 4-(2-hydroxy-1-methyl-ethylamino)-7-β-(D-ribofuranosyl)-furo[3,2-d]pyrimidine; or a pharmaceutically acceptable salt or prodrug thereof.

In one embodiment, the invention excludes compounds of formula I wherein Y is S; when R is —$NH_2$, —OH, —SH, or —$SCH_3$; $R^1$ is hydrogen; and $R^2$ is non-phosphorylated ribose; as well as compounds of formula I wherein Y is 0; when R is —$NH^2$; $R^1$ is hydrogen; and $R^2$ is non-phosphorylated ribose.

In another embodiment the invention excludes compounds of formula I wherein Y is S; R is —$NH_2$, —OH, —SH, or —$SCH_3$; $R^1$ is hydrogen; and $R^2$ is ribose; as well as compounds of formula I wherein Y is 0; R is —$NH_2$; $R^1$ is hydrogen; and $R^2$ is ribose. In another embodiment, the invention excludes compounds of formula I wherein R is —SH, —OH, —S-alkyl, —O-alkyl, or $NR_3R_4$; $R_3$ and $R_4$ are each H or alkyl; and $R^2$ has the following formula:

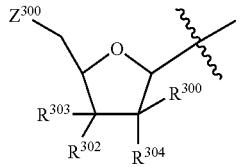

wherein: one of $R^{300}$ and $R^{304}$ is H and the other is H or OH; $R^{302}$ is OH, alkyl-O—, alkylC(=O)O—, alkyl-S—, or alkylC(=O)—S—; $R^{303}$ is H; and $Z^{300}$ is OH, alkyl-O—, alkylC(=O)O—, alkyl-S—, or alkylC(=O)—S—.

In another embodiment, the invention excludes compounds of formula I wherein $R^2$ has the following formula:

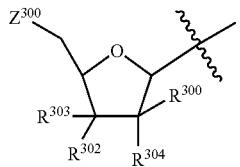

wherein: one of $R^{300}$ and $R^{304}$ is H and the other is H or OH; $R^{302}$ is OH, alkyl-O—, alkylC(=O)O—, alkyl-S—, or alkylC(=O)—S—; $R^{303}$ is H; and $Z^{300}$ is OH, alkyl-O—, alkylC(=O)O, alkyl-S—, or alkylC(=O)—S—.

In one embodiment of the invention $R^2$ is:

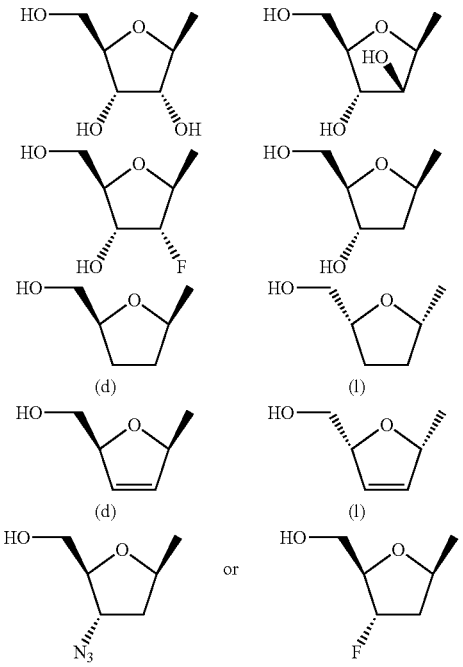

In one embodiment of the invention $R^2$ is:

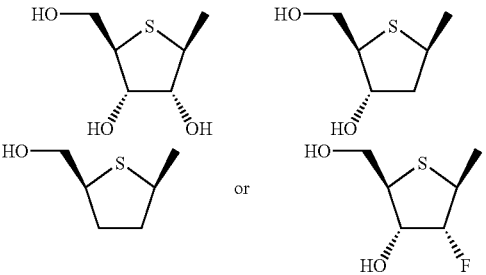

In one embodiment of the invention $R^2$ is:

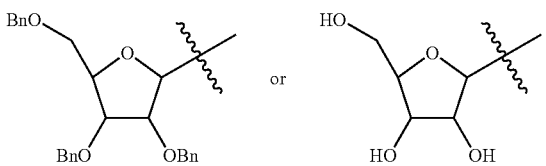

In one embodiment of the invention $R^3$ is H.

In one embodiment of the invention the compound of formula I has the following formula:

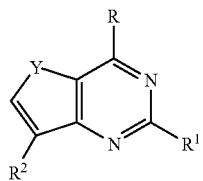

wherein:

Y is O or S;

R is OR$_3$, SR$_3$, NR$_3$R$_4$, NR$_3$NR$_4$R$_5$, alkyl, substituted alkyl, alkenyl, substituted alkenyl, alkynyl, substituted alkynyl, aryl, substituted aryl, (CH$_2$)$_n$—CH(NHR$_3$)CO$_2$R$_4$, Cl, F, Br, I, CN, COOR$_3$, CONR$_3$R$_4$, NHC(=NR$_3$)NHR$_4$, NR$_3$OR$_4$, NR$_3$NO, NHCONHR$_3$, NR$_3$N=NR$_4$, NR$_3$N=CHR$_4$, NR$_3$C(O)NR$_4$R$_5$, NR$_3$C(S)NR$_4$R$_5$, NR$_3$C(O)OR$_4$, CH=N—OR$_3$, NR$_3$C(=NH)NR$_4$R$_5$, NR$_3$C(O)NR$_4$NR$_5$R$_6$, O—C(O)R$_3$, OC(O)—OR$_3$, ONH—C(O)O-alkyl, ONHC(O)O-aryl, ONR$_3$R$_4$, SNR$_3$R$_4$, S—ONR$_3$R$_4$, or SO$_2$NR$_3$R$_4$ n is 0-5;

R$^1$ is H, NR$_3$R$_4$, Cl, F, OR$_3$, SR$_3$, NHCOR$_3$, NHSO$_2$R$_3$, NHCONHR$_3$, CN, alkyl, aryl, ONR$_3$R$_4$, or NR$_3$C(O)OR$_4$;

R$^2$ is ribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose; and R$_3$, R$_4$, R$_5$, and R$_6$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, SO$_2$-alkyl and NO; or R$_3$ and R$_4$ together with the nitrogen to which they are attached form a pyrrolidino, piperidino, piperazino, azetidino, morpholino, or thiomorpholino ring; or R$_4$ and R$_5$ together with the nitrogen to which they are attached form a pyrrolidino, piperidino, piperazino, azetidino, morpholino, or thiomorpholino ring;

or a pharmaceutically acceptable salt or prodrug thereof.

In one embodiment of the invention the compound of formula I has the formula:

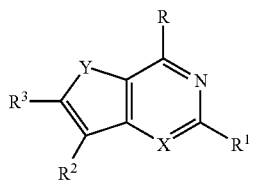

wherein

X=N or CH;

Y=O, S or N—R$^4$;

R=OR$^5$, NHR$^4$, NR$^4$R$^5$, NHNHR$^4$, NR$^4$NHR$^5$, SR$^5$, alkyl, aryl, Cl, NR$^4$OR$^5$, NR$^4$NO, or NHCONHR$^4$;

R=H, NHR$^4$, Cl, F, OR$^4$, SR$^4$, NHCOR$^4$, NHSO$_2$R$^4$, NHCONHR$^4$, CN, alkyl, aryl, or NR$^4$R$^5$;

R$^2$=ribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose;

R$^3$=H, alkyl, aryl, F, Cl, CN, CO$_2$H or NH$_2$;

R$^4$=H, OH, alkyl, aryl, —COO-alkyl, CONH$_2$, CONH-alkyl, O—C(O)-alkyl, O—C(O)-aryl or alkoxy;

R$^5$=alkyl, aryl, OH or alkoxy.

In one embodiment of the invention the compound of formula I has the formula:

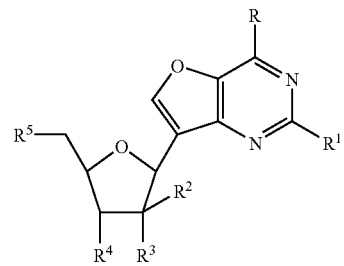

wherein:

R is OR$_a$, SR$_a$, NR$_e$R$_f$, NR$_a$NR$_b$R$_c$, alkyl, alkenyl, alkynyl, aryl, (CH$_2$)$_n$NR$_a$R$_b$, (CH$_2$)$_n$OR$_a$, C(=NR$_a$)NR$_b$R$_c$, (CH$_2$)$_n$—CH(NHR$_a$)CO$_2$R$_b$, (CH$_2$)$_n$—S-alkyl, (CH$_2$)$_n$—S-aryl, Cl, F, Br, I, CN, COOR$_a$, CONR$_a$R$_b$, NHC(=NR$_a$)NHR$_b$, NR$_a$OR$_b$, NR$_a$NO, NHCONHR$_a$, NR$_a$N=NR$_b$, NR$_a$N=CHR$_b$, NR$_a$C(O)NR$_b$R$_c$, NR$_a$C(S)NR$_b$R$_c$, NR$_a$C(O)OR$_b$, CH=N—OR$_a$, NR$_a$C(=NH)NR$_b$R$_c$, NR$_a$C(O)NR$_b$NR$_c$R$_d$, O—C(O)R$_a$, OC(O)—OR$_a$, ONH—C(O)O-alkyl, ONHC(O)O-aryl, ONR$_a$R$_b$, SNR$_a$R$_b$, S—ONR$_a$R$_b$, or SO$_2$NR$_a$R$_b$;

n is 0, 1, 2, 3, 4, or 5;

R$^1$ is H, NR$_a$R$_b$, Cl, F, OR$_a$, SR$_a$, NHCOR$_a$, NHSO$_2$R$_a$, NHCONHR$_a$, CN, alkyl, aryl, ONR$_a$R$_b$, or NR$_a$C(O)OR$_b$;

R$^2$ is H and R$^3$ is OH; or R$^2$ is OH and R$^3$ is H;

R$^4$ is OH, alkyl-O—, alkylC(=O)O, alkyl-S—, or alkylC(=O)—S—;

R$^5$ is OH, alkyl-O—, alkylC(=O)O, alkyl-S—, or alkylC(=O)—S—

R$_a$, R$_b$, R$_c$, and R$_d$ are independently selected from the group consisting of H, alkyl, alkenyl, alkynyl, cycloalkyl, heterocyclic, aryl, acyl, SO$_2$-alkyl and NO; or R$_a$ and R$_b$ together with the nitrogen to which they are attached form a pyrrolidino, piperidino, piperazino, azetidino, morpholino, pyrrolino, or thiomorpholino ring; or R$_b$ and R$_c$ together with the nitrogen to which they are attached form a pyrrolidino, piperidino, piperazino, azetidino, morpholino, pyrrolino, or thiomorpholino ring;

R$_e$ is alkyl, alkenyl, alkynyl, cycloalkyl, heterocyclic, aryl, acyl, SO$_2$-alkyl or NO; and R$_f$ is H, alkyl, alkenyl, alkynyl, cycloalkyl, heterocyclic, aryl, acyl, SO$_2$-alkyl and NO; or R$_e$ and R$_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, N$_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic. Representative compounds of this formula were found to be particularly useful for treating HCV.

Prodrugs

The term "prodrug" as used herein refers to a compound that can be metabolized in vivo to provide a compound of formula I. Thus prodrugs include compounds that can be prepared by modifying one or more functional groups in a compound of formula I to provide a corresponding compound that can be metabolized in vivo to provide a compound of formula I. Such modifications are known in the art. For example, one or more hydroxy groups or amine groups in a compound of formula I can be acylated with alkyl-C(=O)- groups or with residues from amino acids to provide a prodrug. Alternatively, one or more pendent hydroxyl groups from a mono-, di-, or tri-phosphate functionality in a compound of formula I can be converted to an alkoxy, or aryloxy group.

In one embodiment, the term prodrug includes a compound wherein one or more hydroxy groups on a nucleoside sugar group (e.g. a 2', 3', or 5' hydroxy group) have been converted to a group that can be metabolized in vivo to provide a compound of formula I. For example, the invention provides a compound wherein one or more hydroxy groups on a nucleoside sugar group (e.g. a 2', 3', or 5' hydroxy group) have been converted to an acyloxy, acylamino or R—O group, wherein R is a carboxy-linked amino acid.

In one embodiment, the term prodrug includes a compound wherein one or more pendent hydroxyl groups from a mono-, di-, or tri-phosphate functionality in a compound of formula I is converted to a group $R_y$—O—; wherein each $R_y$ is independently a 1-20 carbon branched or unbranched, saturated or unsaturated chain, wherein one or more (e.g. 1, 2, 3, or 4) of the carbon atoms is optionally replaced with —O— or —S— and wherein one or more of the carbon atoms is optionally substituted with oxo (=O) or thioxo (=S) (See Lefebvre et al., J. Med. Chem. 1995, 38, 3941-50).

In another embodiment, the term prodrug includes a compound wherein one or more pendent hydroxyl groups from a mono-, di-, or tri-phosphate functionality in a compound of formula I is converted to a group $R_z$—N—; wherein each $R_z$ is a residue of an amino acid. Thus, in the methods of treatment of the present invention, the term "administering" includes administration of a compound of formula I, as well as administration of a prodrug which converts to a compound of formula I or a salt thereof in vivo. Conventional procedures for the selection and preparation of prodrug derivatives are described, for example, in "Design of Prodrugs", ed. H. Bundgaard, Elsevier, 1985; and in International Patent Application Publication Number WO 2005/084192. A variety of prodrugs are also described in International Patent Application Number PCT US2004/013063, which was published as International Publication Number WO 2004/096286.

In another embodiment the prodrug comprises one of more groups of formula:

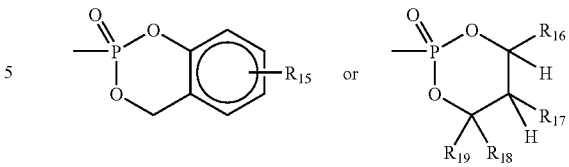

wherein:

$R_{15}$ is H, alkyl, aryl, cycloalkyl, heteroaryl, heterocyclic, and an amino acid;

$R_{16}$ is H, monocyclic aryl, or monocyclic heteroaryl; and $R_{17}$ is H, halogen, CN, —CO—$R_{20}$, —CON($R_{21}$)$_2$, —CO$_2R_{20}$, —SO$_2R_{20}$, —SO$_2$N($R_{21}$)$_2$, —O$R_{21}$, —S$R_{21}$, —$R_{21}$, —N($R_{21}$)$_2$, —O—CO$R_{20}$, —O—CO$_2R_{20}$, —SCO$R_{20}$, —S—CO$_2R_{20}$, —NHCO$R_{21}$, —NHCO$_2R_{21}$, —(CH$_2$)$_p$—O$R_{22}$, or —(CH$_2$)$_p$—S$R_{22}$; or $R_{16}$ and $R_{17}$ are connected via an additional 3-5 atoms to form a cyclic group, optionally containing one heteroatom, that is fused to an aryl group at the beta and gamma position to the 0 attached to the phosphorus; or $R_{17}$ and $R_{18}$ are connected as described below;

$R_{18}$ and $R_{19}$ are each independently H, alkyl, aryl, aralkyl, monocyclic aryl or monocyclic heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, aralkyl, monocyclic aryl or monocyclic heteroaryl; and $R_{20}$ is alkyl, aryl, or arylalkyl;

$R_{21}$ is H, alkyl, aryl, or arylalkyl;

$R_{22}$ is H or lower acyl;

p is an integer from 2-3;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

Prodrug forms of a compound bearing various nitrogen functions (amino, hydroxyamino, amide, etc.) may include the following types of derivatives where each $R_p$ group individually may be hydrogen, alkyl, aryl, alkenyl, alkynyl, heterocycle, alkylaryl, aralkyl, aralkenyl, aralkynyl, cycloalkyl or cycloalkenyl groups as defined earlier.

(a) Carboxamides, represented as —NHC(O)$R_p$
(b) Carbamates, represented as —NHC(O)O$R_p$
(c) (Acyloxy)alkyl Carbamates, represented as NHC(O) OROC(O)$R_p$
(d) Enamines, represented as —NHCR(=CHCO$_2R_p$) or —NHCR(=CHCON$R_pR_p$)
(e) Schiff Bases, represented as —N=CR$_pR_p$
(f) Mannich Bases (from carboximide compounds), represented as RCONHCH$_2$NR$_pR_p$ Preparations of such prodrug derivatives are discussed in various literature sources (examples are: Alexander et al., J. Med. Chem. 1988, 31, 318; Aligas-Martin et al., PCT WO0041531, p. 30).

Prodrug forms of carboxyl-bearing compounds include esters (—CO$_2$R$_m$) where the R$_m$ group corresponds to any alcohol whose release in the body through enzymatic or hydrolytic processes would be at pharmaceutically acceptable levels. Another prodrug derived from a carboxylic acid form of the disclosure may be a quaternary salt type of structure described by Bodor et al., J. Med. Chem. 1980, 23, 469.

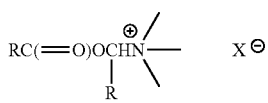

Synthetic Processes

Processes for preparing compounds of formula I, or pharmaceutically acceptable salts or prodrugs thereof, as well as processes for preparing intermediate compounds that can be used to prepare compounds of formula I or pharmaceutically acceptable salts or prodrugs thereof are provided as further embodiments of the invention. For example in one embodiment the invention provides a method for preparing a pharmaceutically acceptable salt of compound of formula I comprising converting a corresponding compound of formula I to the salt.

In another embodiment the invention provides a method for preparing a prodrug of a compound of formula I comprising converting a corresponding compound of formula I to the prodrug.

In another embodiment the invention provides a method for preparing a compound of formula I, comprising deprotecting a corresponding compound of formula I that comprises one or more protecting groups to provide the compound of formula I.

Isomers and Physical Forms

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixtures thereof, of a compound of the invention (e.g. a compound of formula I), which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-viral activity using the standard tests described herein, or using other similar tests which are well known in the art. Although the invention includes all isomeric forms of the compounds described herein, one embodiment of the invention provides compounds having the absolute stereochemistry depicted in the Examples hereinbelow.

It will be appreciated that sugars can exist in α- and β-forms. The invention includes compounds of formula I comprising sugars in both α- and β-forms. In one embodiment, the sugars are in the C-1 β-form.

For example, it would be known in the field of chemistry that a compound of the following formula:

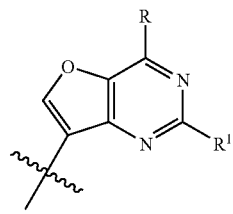

wherein R is OH would form a tautomer of the following formula:

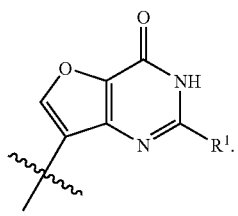

Accordingly, the invention includes all tautometric forms of the compounds of formulae I.

Pharmaceutical Compositions, Modes of Administration and Methods of Treatment

The present disclosure provides compounds of the general formula (I) as detailed above which are inhibitors of HCV DNA and/or RNA polymerases. Various forms of DNA and RNA viral polymerases are inhibited by the compounds disclosed, such as but not limited to HCV RdRps. The compounds of the present disclosure therefore have utility in treating and/or preventing HCV infections in a host and in treatment and/or preventing a variety of disease states and/or conditions caused by or related to HCV infections. In one embodiment, the compounds are useful in the above mentioned treating and/or preventing by inhibiting a HCV RNA and DNA polymerases.

The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds described in the instant disclosure can be administered by any conventional method available for use in conjunction with pharmaceuticals, either as individual therapeutic agents or in combination with additional therapeutic agents.

The compounds described are administered in a pharmaceutically effective amount. The pharmaceutically effective amount of the compound and the dosage of the pharmaceutical composition administered will, of course, vary depending upon known factors, such as the pharmacodynamic characteristics of the particular agent and its mode and route of administration; the age, health and weight of the recipient; the severity and stage of the disease state or condition; the kind of concurrent treatment; the frequency of treatment; and the effect desired.

A daily dosage of active ingredient can be expected to be about 0.001 to 1000 milligrams (mg) per kilogram (kg) of body weight per day. In one embodiment, the total amount is between about 0.1 mg/kg and about 100 mg/kg of body weight per day; in an alternate embodiment between about 1.1 mg/kg and about 50 mg/kg of body weight per day; in yet another alternate embodiment between 0.1 mg/kg and about 30 mg/kg of body weight per day. The above described amounts may be administered as a series of smaller doses over a period of time if desired. The pharmaceutically effective amount can be calculated based on the weight of the parent compound to be delivered. If the salt or prodrug exhibits activity in itself, the pharmaceutically effective amount can be estimated as above using the weight of the salt or prodrug, or by other means known to those skilled in the art. The dosage of active ingredient may be given other than daily if desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

Dosage forms of the pharmaceutical compositions described herein (forms of the pharmaceutical compositions suitable for administration) contain from about 0.1 mg to about 3000 mg of active ingredient (i.e. the compounds disclosed) per unit. In these pharmaceutical compositions, the active ingredient will ordinarily be present in an amount of about 0.5-95% weight based on the total weight of the composition. Multiple dosage forms may be administered as part of a single treatment. The active ingredient may be administered to achieve peak plasma concentrations of the active ingredient of from about 0.2 to 70 µM, or from about 1.0 to 10 µM.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation via the pulmonary system, such as by propellant based metered dose inhalers or dry powders inhalation devices. Other dosage forms are potentially possible such as administration transdermally, via patch mechanisms or ointment.

Formulations suitable for oral administration can include (a) liquid solutions, such as a pharmaceutically effective amount of the compound dissolved in diluents, such as water, saline, or orange juice; (b) capsules, sachets, tablets, lozenges, and troches, each containing a predetermined pharmaceutically effective amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl .beta.-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include pastilles comprising the active ingredient in an inert base, such as gelatin and glycerin, or sucrose and acacia, as well as creams, emulsions, and gels containing, in addition to the active ingredient, such carriers as are known in the art. Furthermore, transdermal patches can be prepared using methods known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an patient are available, and, although more than one route can be used to administer a particular compound, a particular route can provide a more immediate and more effective reaction than another route.

Useful embodiments of pharmaceutical dosage forms for administration of the compounds according to the present invention can be illustrated as follows.

A large number of hard-shell capsules are prepared by filling standard two-piece hard gelatine capsules each with 100 mg of powdered active ingredient, 150 mg of lactose, 50 mg of cellulose and 6 mg of magnesium stearate.

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate release tablets/capsules are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

In one embodiment, the teachings of the present disclosure provide for the use of such pharmaceutical compositions and medicaments in a method of treating a HCV infection or treating a disease state and/or condition caused by or related to such infection. Such treatment need not be complete to be useful.

The methods of treating HCV infection or a disease state and/or condition caused by or related to said infection may further comprise administering a therapeutically effective amount of a compound of the present invention in combination with a therapeutically effective amount of an immune modulator, an interferon inducer (see Kurimoto et. al. *Bioorganic and Med. Chem*, 2003, 11, 5501-5508; and Hirota et. al. *J. Med. Chem.* 2002, 45, 5419-5422), or another anti-viral agent which, in particular, may be active against HCV. Agents active against HCV include, but are not limited to, ribavirin, levovirin, viramidine, thymosin alpha-1, an inhibitor of HCV NS3 serine protease, an inhibitor of inosine monophosphate-dehydrognease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a, interferon-α2b, a consensus interferon, and a purified interferon-α product.

The ability of a compound to inhibit an HCV polymeras can be evaluated using known assays. The ability of a compound to inhibit HCV NS5B polymerase can be evaluated using the following assay.

HCV NS5B Polymerase Assay

Antiviral activity of the test compounds can be assessed (Okuse et al., Antiviral Res. 2005, 65, 23-34) in the stably HCV RNA-replicating cell line, AVA5, derived by transfection of the human hepatoblastoma cell line, Huh7 (Blight et al., Sci. 2000, 290, 1972). Compounds are added to dividing cultures once daily for three days. Media is changed with each addition of compound. Cultures generally started the assay at 30-50% confluence and reach confluence during the last day of treatment. Intracellular HCV RNA levels and cytotoxicity are assessed 24 hours after the last dose of compound.

Triplicate cultures for HCV-RNA levels (on 48-well and 96-well plates) and cytotoxicity (on 96-well plates) are used. A total of six untreated control cultures, and triplicate cultures treated with α-interferon and ribavirin can serve as positive antiviral and toxicity controls.

Intracellular HCV RNA levels can be measured using a conventional blot hybridization method in which HCV RNA levels are normalized to the levels of B-actin RNA in each individual culture (Okuse et al., Antivir. Res. 2005, 65, 23-34). Cytotoxicity is measured using a neutral red dye uptake assay (Korba and Gerin, Antivir. Res. 1992, 19, 55). HCV RNA levels in the treated cultures are expressed as a percentage of the mean levels of RNA detected in untreated cultures. Representative compounds of the invention that were tested in the above assay typically demonstrated an $IC_{50}$ of less than about 100 μm.

Compound Synthesis

Compounds of formula I can be prepared using synthetic intermediates and synthetic procedures that are known, or they can be prepared using the synthetic intermediates and synthetic procedures identified in the Schemes and Examples herein. The following abbreviations are used herein.

| Tr: | trityl |
|---|---|
| Bn: | benzyl |
| TBDPS: | tert-butyldiphenylsilyl |
| m-CPBA: | 3-chloroperoxybenzoic acid |
| TFA: | trifluoroacetic acid |
| TBDMSCl: | tert-butyldimethylsilyl chloride |
| DMF: | dimethylformamide |
| THF: | tetrahydrofuran |
| LDA: | lithium diisopropylamine |
| TEAB: | triethylammonium bicarbonate |
| mMTrCl: | monomethoxytrityl chloride |
| DMAP: | dimethylaminopyridine |
| DEAE: | diethylaminoethyl-sepharose |
| CMA-80: | Chloroform 80:MeOH 18:$NH_4OH$:2 |
| CMA-50: | Chloroform 50:MeOH 40:$NH_4OH$:10 |
| Bz: | benzoyl |
| BnBr: | benzyl bromide |
| LiHMDS: | lithium hexamethyldisalazane |
| TBDPSCl: | tert-butyldiphenylsilyl chloride |
| DMSO: | dimethylsulfoxide |
| RMgBr: | alkyl magnesium bromide |
| DIBAL: | diisobutylaluminum hydride |
| DBN: | 1,5-diazabicyclo[4.3.0]non-5-ene |
| DBU: | 1,8-diazabicyclo[5.4.0]undec-7-ene |
| MeMgBr: | methylmagnesium bromide |

Representative compounds can be prepared using the synthetic procedures illustrated in Schemes 1-9 below.

Scheme 1.

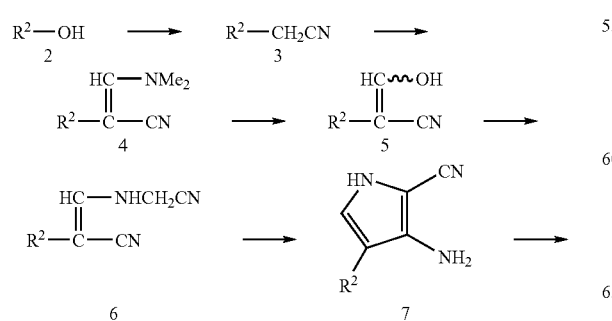

Scheme 2.

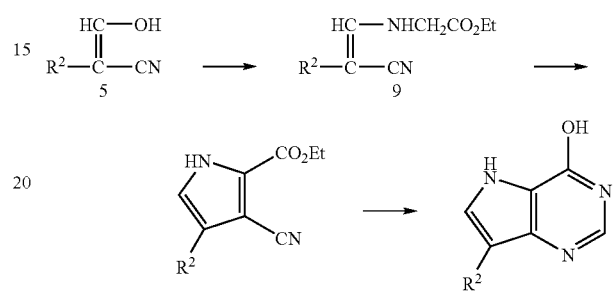

Scheme 3.

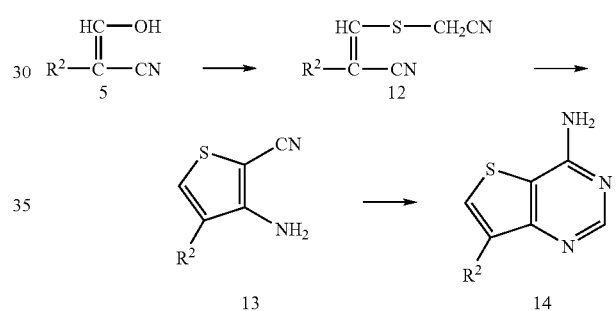

Scheme 4.

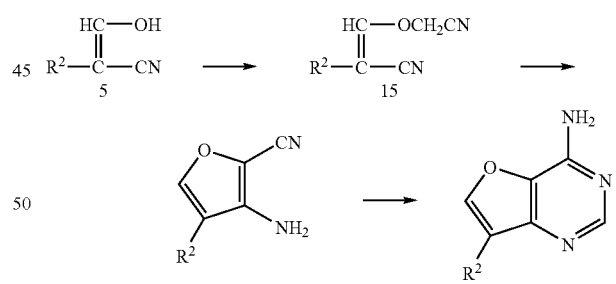

Scheme 5.

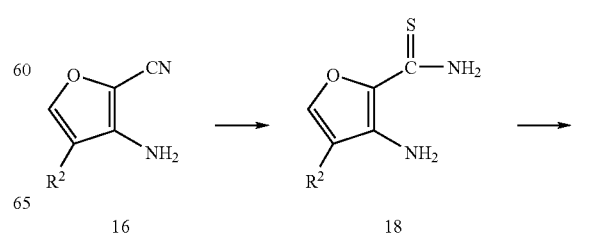

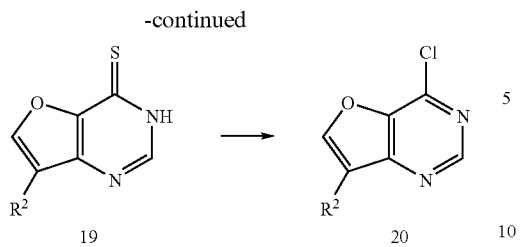
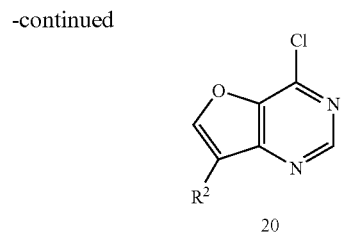
Scheme 6.
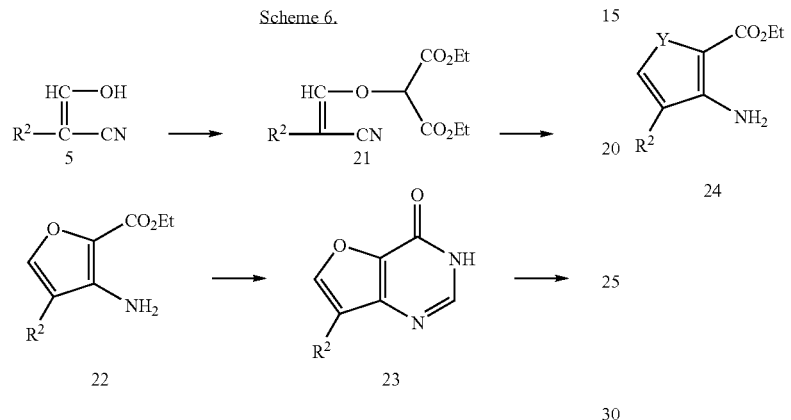
Scheme 7.
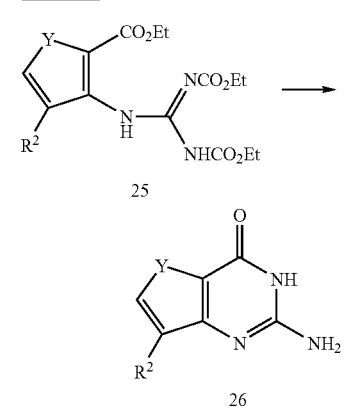
Scheme 8.
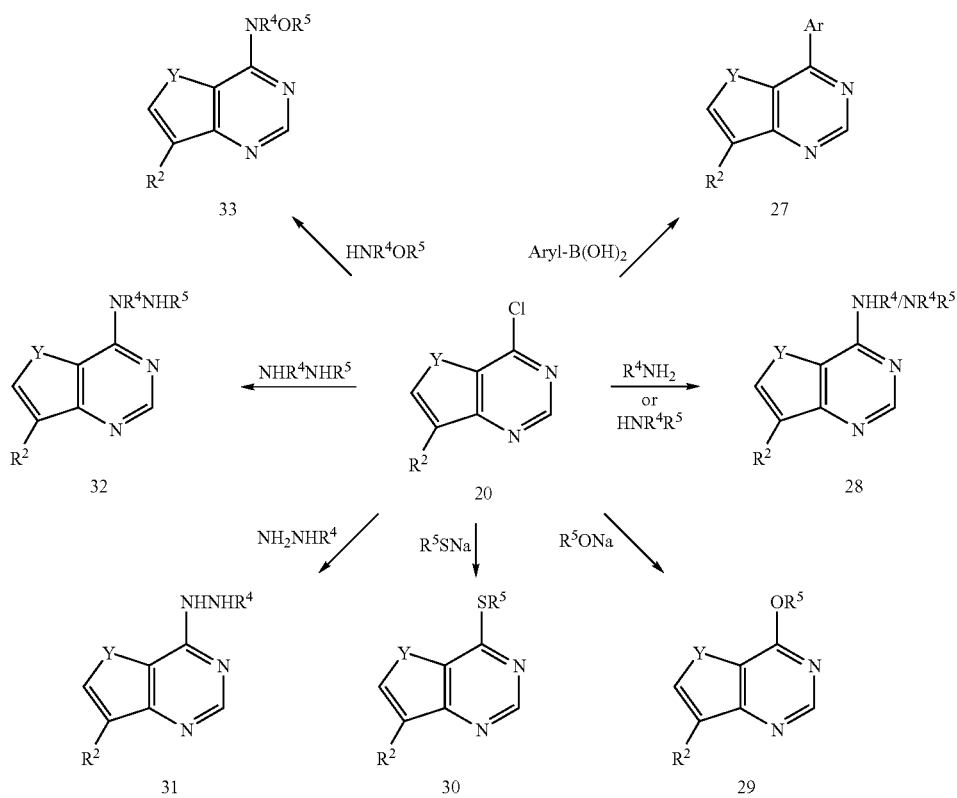

Scheme 9.

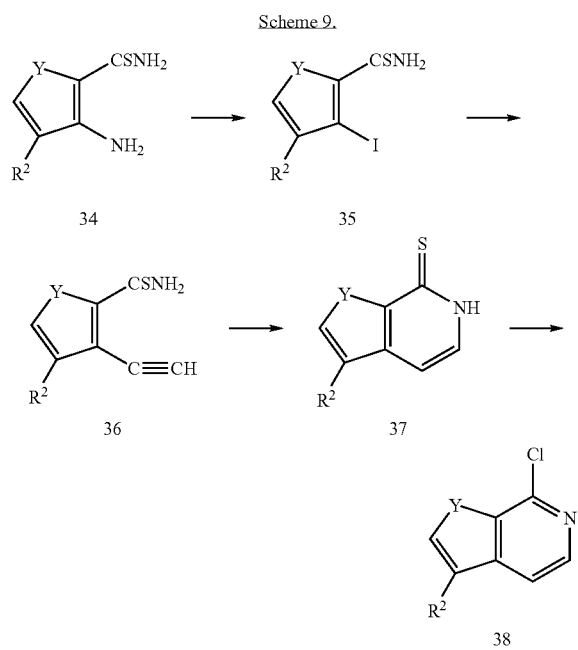

Cl is converted to the groups described in Scheme 8.

Appropriately protected starting materials 2 or 3 (Scheme 1), are either commercially available or can be prepared from the known literature procedures.

The description of synthetic schemes 1-9 follows.

Scheme 1, Preparation of Compounds of Formula I wherein X=N, Y=NH, R=NH$_2$, R$^1$=H, R$^2$=Any Group Described, and R$^3$=H:

Compound 3 (prepared from literature procedures or from 2 by the reaction of NCCH$_2$P(O)(OEt)$_2$ and sodium hydride), is reacted with Brederick's reagent [tert-butoxybis(dimethylamino)methane] to give 4, which on acidic hydrolysis with acetic acid or trifluoroacetic acid generates compound 5. Compound 5 is further reacted with amino acetonitrile to give 6, where NH is protected with methoxycarbonyl and cyclized in the presence of a base, such as DBU, and then NH is deprotected with sodium carbonate in methanol to give desired cyclized product 7. The isomers of the cyclized product are separated by chromatography or crystallization. Further cyclization of desired 7 with formamidine acetate and deprotection of the hydroxyl or amino functionalities in R$^2$ produces the desired targets 8.

Scheme 2, Preparation of Compounds of Formula I wherein X=N, Y=NH, R=OH, R$^1$=H, R$^2$=Any Group Described, and R$^3$=H:

Compound 5 is reacted with NH$_2$CH$_2$CO$_2$C$_2$H$_5$ to give 9, which is then cyclized with a base, such as DBU to give compound 10. The isomers of the cyclized product are separated by chromatography or crystallization. Further cyclization of desired 10 with formamidine acetate followed by deprotection of the hydroxyl or amino functionalities in R$^2$ produces the desired target 11.

Scheme 3, Preparation of Compounds of Formula I wherein X=N, Y=S, R=NH$_2$, R$^1$=H, R$^2$=Any Group Described, and R$^3$=H:

Compound 5 is treated with methanesulfonyl chloride in the presence of base and then reacted with acetylthioacetonitrile and sodium carbonate to give compound 12, which on heating cyclizes to 13. The isomers of the cyclized product are separated by chromatography or crystallization. Further cyclization of desired 13 with formamidine acetate followed by deprotection of the hydroxyl or amino functionalities in R$^2$ produces the desired target 14.

Scheme 4, Preparation of Compounds of Formula I wherein X=N, Y=O, R=NH$_2$, R$^1$=H, R$^2$=Any Group Described, and R$^3$=H:

Compound 5 is treated with chloroacetonitrile in the presence of potassium fluoride and 18-crown-6 to generate 15, which on treatment with LDA cyclizes to desired 16. The isomers of the cyclized product are separated by chromatography or crystallization. Further cyclization of desired 16 with formamidine acetate followed by deprotection of the hydroxyl or amino functionalities in R$^2$ produces the desired target 17.

Scheme 5, Preparation of Compounds of Formula I wherein X=N, Y=O, R=Cl, SH or S-alkyl, R$^1$=H, R$^2$=Any Group Described, and R$^3$=H:

Compound 16 is treated with H$_2$S gas to produce thioamide 18, which on cyclization with formamidine acetate gives compound 19. Further treatment of 19 with POCl$_3$ generates protected 20, which is a common intermediate for various R-substituted compounds. Compounds 19 and 20, if deprotected produces the targets 20, with R=SH and Cl. Compound 19 on treating with alkyl halides may produce S-alkyl compounds also.

Scheme 6, Preparation of Compounds of Formula I wherein X=N, Y=O, R=Cl, R$^1$=H, R$^2$=Any Group Described, and R$^3$=H:

Compound 20 alternatively is produced through this Scheme. The reaction of the sodium salt of compound 5 with bromo or chlorodiethylmalonate generates 21, which on base treatment cyclizes to give 22. The isomers of the cyclized product are separated by chromatography or crystallization. Further cyclization of desired 22 with formamidine acetate gives 23, which on treatment with POCl$_3$ generates protected 20, which is a common intermediate for various R-substituted compounds. Compound 23, if deprotected produces the targets, with R=OH. Compound 23 on treating with alkyl halides may produce O-alkyl compounds also.

Scheme 7, Preparation of Compounds of Formula I wherein X=N; Y=O, S or NH; R=OH; R$^1$=NH$_2$, R$^2$=Any Group Described, and R$^3$=H:

Compound 24 is treated with N,N'-bis-methoxycarbonyl-S-methylthiourea in the presence of mercury (II) chloride to generate 25, which on treatment with base for cyclization followed by deprotection of the hydroxyl or amino functionalities in R$^2$ produces the desired target 26.

Scheme 8, Preparation of Compounds of Formula I wherein X=N; Y=O, S or NH; R=NHR$^4$/NR$^4$R$^5$, Ar, NR$^4$OR$^5$, NR$^4$NHR$^5$, NHNHR$^4$, SR$^5$ or OR$^5$; R$^1$=H, R$^2$=Any Group Described, and R$^3$=H:

Compound 20, when Y=O is prepared as described in Scheme 5 and 6. When Y=S or NH, these are prepared from the corresponding 13, 7 and 18 by the same methods used in Schemes 5 and 6. Compound 20 on treatment with i) amines, R$^4$NH$_2$ or R$^4$R$^5$NH produces 28; ii) aryl boronic acids under Suzuki coupling conditions generates 27; iii) alkoxyamines, HNR$^4$OR$^5$ gives 33; iv) di-substituted hydrazines, HNR$^4$NHR$^5$ produces 32; v) mono-substituted hydrazines, NH$_2$NHR$^4$ gives 31; vi) thioalkoxide, R$^5$SNa generates 30; and vii) alkoxides, R$^5$ONa produces 29. The hydroxyl or amino functionalities in $R^2$ of these compounds are deprotected under suitable conditions to afford the appropriate targets.

Scheme 9, Preparation of Compounds of Formula I wherein X=CH, Y=O, NH or S, R=Cl or the substituents as described in Scheme 8, $R^1$=H, $R^2$=Any Group Described, and $R^3$=H:

Compound 34, when Y=O is the same compound as 18 in Scheme 5. Compound 34 when Y=NH and S, are prepared from 7 and 13 by treatment with $H_2S$ gas. Compound 34 is converted to 35 by treating with $(CH_3)_2CH(CH_2)_2ONO$ and diiodomethane and iodo group of 35 is displaced with acetylenic group to generate 36 by the reaction of trimethylsilylacetylene and $(PhCN)_2PdCl_2$ catalyst followed by acidic treatment. Cyclization of 36 to 37 is achieved through dimethylamine treatment in ethanol followed by aqueous acetic acid. Thio functionality in 37 is converted to chloro with $POCl_3$ to give 38, a common intermediate. Further treatment of 38 with the reagents described in Scheme 8 followed by deprotection of amino and hydroxyl groups in $R^2$ yields the desired targets 38, where Cl is replaced by different groups.

Comopunds can also be prepared as illustrated in the following Schemes A-1 to D-2.

Preparation of $R_2$—$CH_2CN$ Compounds:

Scheme A-1.

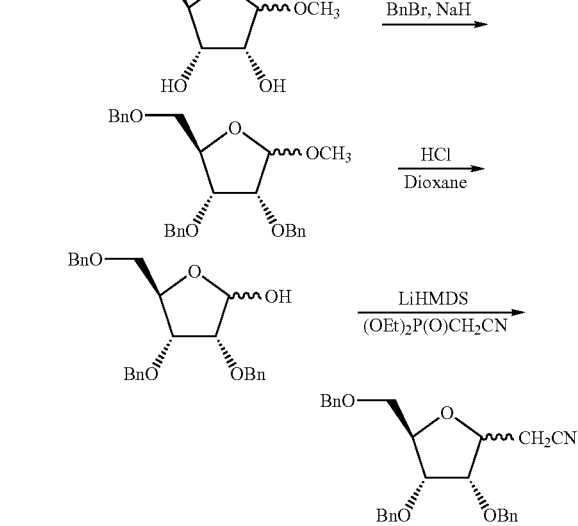

Preparation of Compounds of the Invention from $R_2CH_2CN$ Intermediates

In the following schemes, $R_2$ is a sugar group bearing one or more protecting groups.

Scheme B-1.

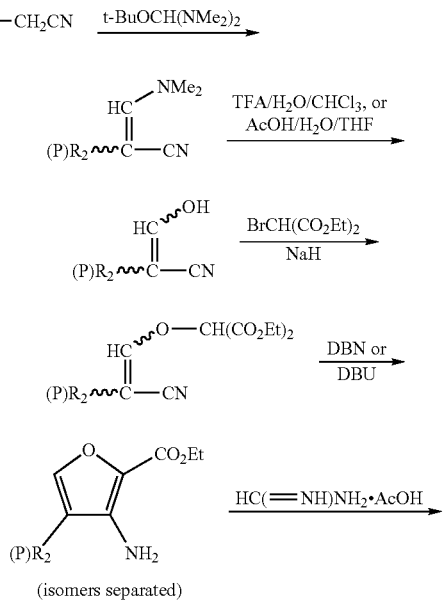

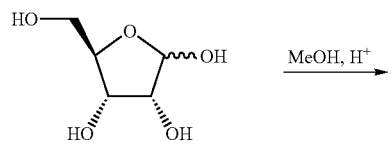

(P) = Protecting group

Scheme B-2.

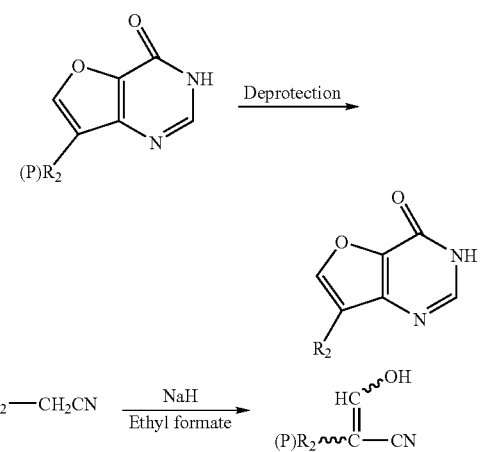

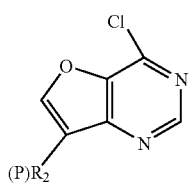

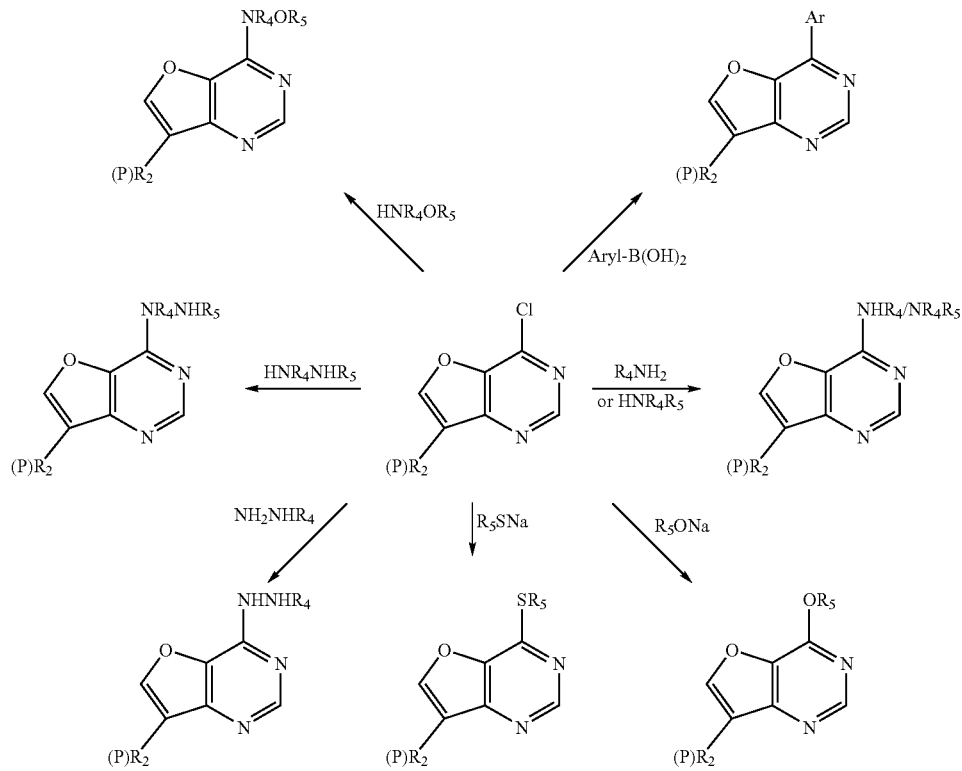
Deprotection of protecting groups in $R_2$ gives the target molecules
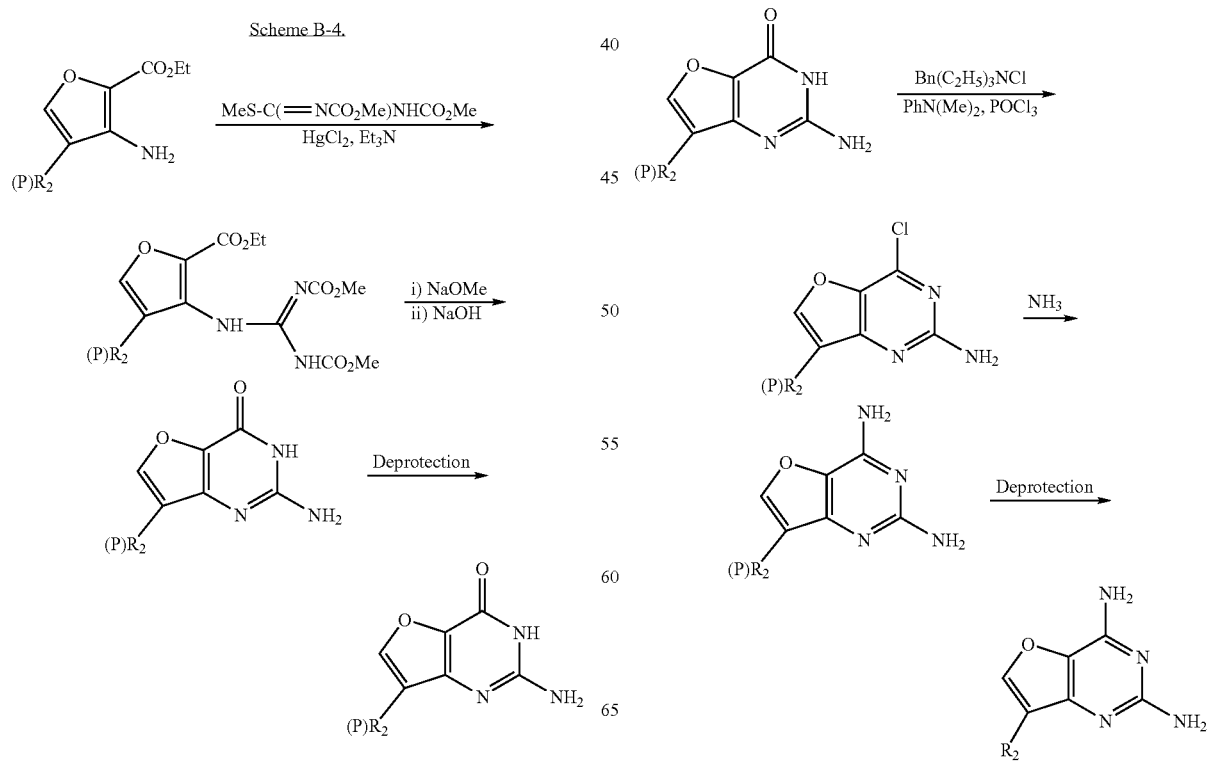

Scheme B-6.

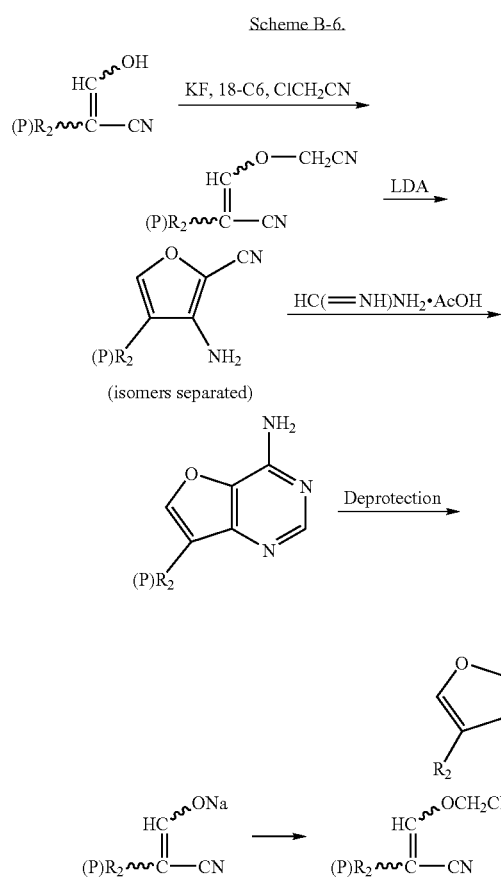

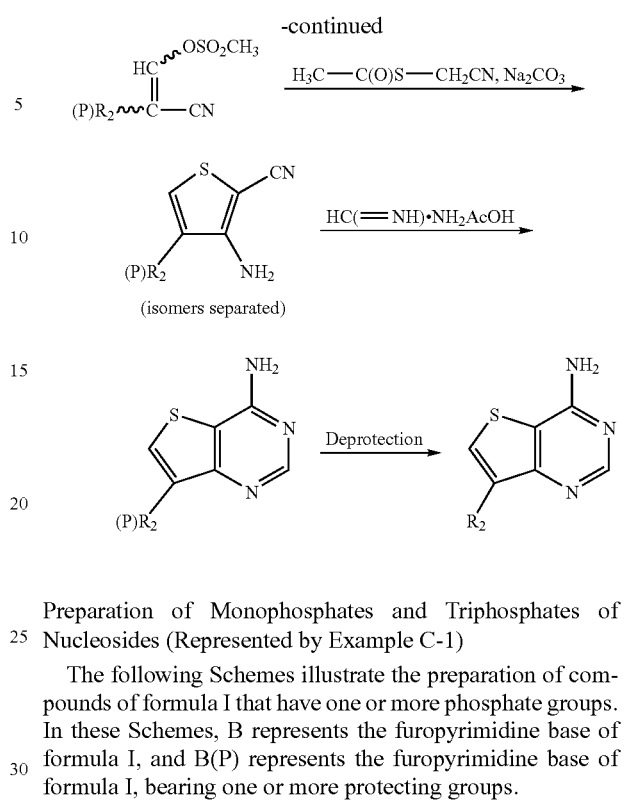

Preparation of Monophosphates and Triphosphates of Nucleosides (Represented by Example C-1)

The following Schemes illustrate the preparation of compounds of formula I that have one or more phosphate groups. In these Schemes, B represents the furopyrimidine base of formula I, and B(P) represents the furopyrimidine base of formula I, bearing one or more protecting groups.

Scheme B-7.

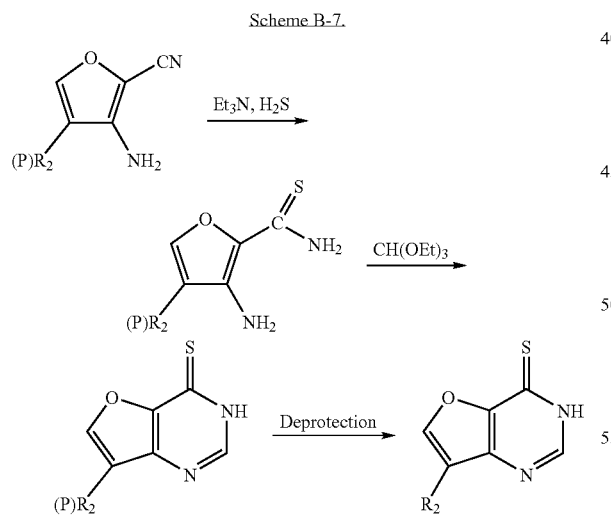

Scheme C-1.

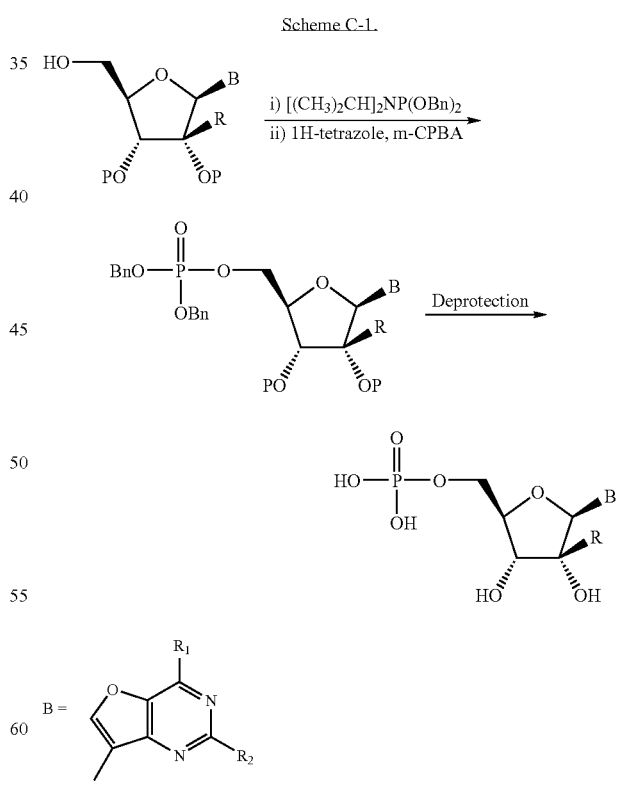

Scheme B-8.

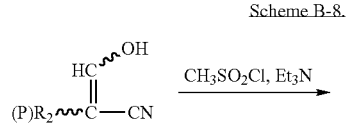

R = H
$R_1$ = OH, $NH_2$, $NHCH_3$, $OCH_3$; $R_2$ = H, $NH_2$
P = Protecting group
m-CPBA = m-chloroperbenzoic acid Scheme C-2.

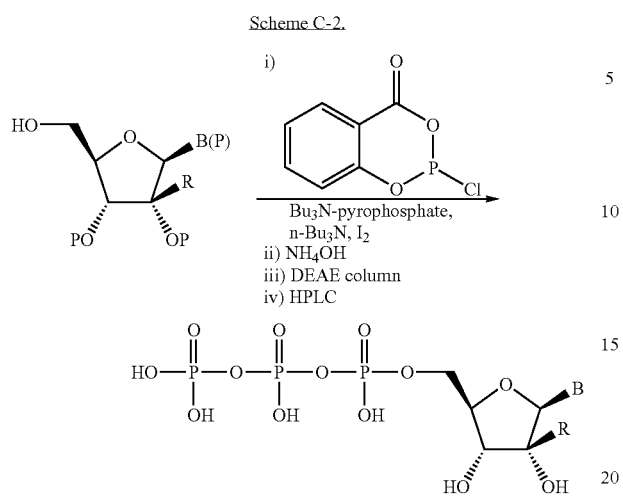

B and R are the same as in Scheme C-1

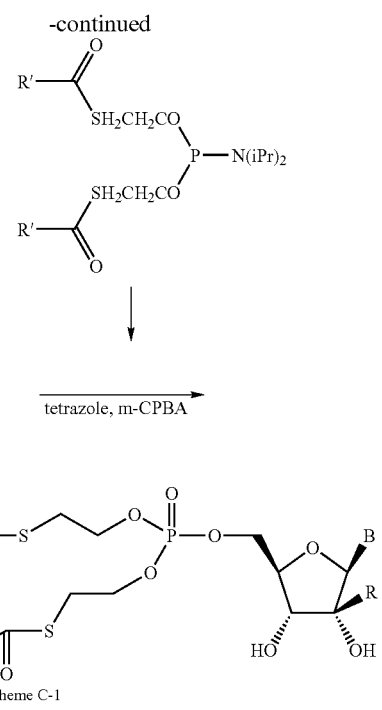

B and R are the same as in scheme C-1
R' = CH$_3$, C(CH$_3$)$_3$

Preparation of Prodrugs

The following Schemes illustrate the preparation of prodrugs of the invention.

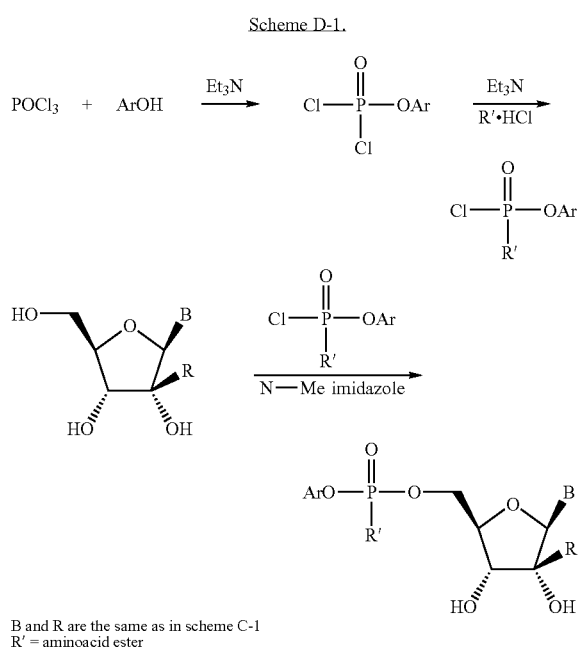

B and R are the same as in scheme C-1
R' = aminoacid ester

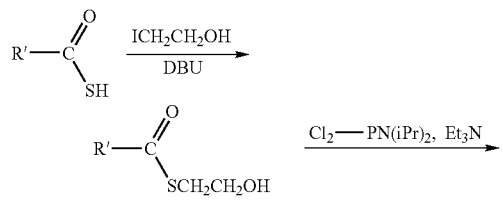

The invention will now be illustrated by the following non-limiting Examples.

EXAMPLE A-1

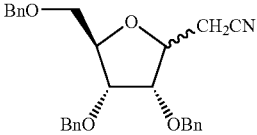

2-(3,4-Bis(benzyloxy)-5-(benzyloxymethyl)-tetrahydrofuran-2-yl)acetonitrile (Scheme A-1)

Step 1: To a solution of D-ribose (61 g, 406.66 mmol) in methanol (1 L) was added conc. sulfuric acid (6.1 mL) and stirred at 4° C. for 16 h. The reaction mixture was neutralized using triethylamine (40 mL), concentrated to dryness and co-distilled twice with 200 mL of toluene to remove trace amount of water. This furnished 72 g of crude O-methyl-D-ribofuranose, which was used as such for next step.

Step 2: To a slurry of NaH (65 g, 60%, 1.626 mol) in DMF (200 mL) was added crude compound from Step 1 (72 g, 406.66 mmol) in DMF (800 mL) over a period of 0.5 h, maintaining the temperature below 5° C. The anion formed was stirred at room temperature for 30 min. Benzyl bromide (219.1 g, 1280.9 mmol) was added dropwise over a period of 1 h maintaining temperature between 0-5° C. The reaction was stirred at room temperature for 12 h (TLC analysis in 30% ethyl acetate/hexane showed complete disappearance of starting material), Was diluted with water (500 mL) and extracted with ethyl acetate (2×1 L). The combined organic extracts were washed twice with water (1 L), brine (500 mL), and dried over MgSO$_4$ and filtered. The filtrate was concentrated under vacuum to furnish crude residue. The crude residue was purified by flash chromatography (silica gel 1 kg), eluting with ethyl acetate in hexanes to furnish 112 g (63.3%) of desired product as an oil. $^1$H NMR (DMSO-d$_6$): δ 7.36-7.27 (m, 15H), 4.92 (s, 1H), 4.66-4.44 (m, 6H), 4.12-4.07 (m, 1H), 3.97 (dd, J=6.78 and 4.5 Hz, 1H), 3.91 (d, J=4.5 Hz, 1H), 3.55 (dd, J=10.73 and 3.4 Hz, 1H), 3.42 (dd, J=10.7 and 6.0 Hz, 1H), 3.21 (s, 3H).

Step 3: To a solution of product from Step 2 (114 g, 262.35 mmol) in dioxane (250 mL) was added 4 N HCl (250 mL) and heated at reflux for 4 h. The reaction mixture was allowed to attain room temperature and diluted with ethyl acetate (1.5 L). The aqueous layer was separated and extracted with ethyl acetate (3×1 L). The organic layers were combined, washed with water (2×500 mL), saturated aqueous NaHCO$_3$ (250 mL), water (500 mL), and brine (250 mL), and dried over MgSO$_4$ and filtered. The filtrate was concentrated under vacuum to furnish crude product. The crude product was purified by flash chromatography (silica gel 1.5 kg, eluting with ethyl acetate in hexanes 0 to 30%) to furnish starting material (9.9 g) and 85.3 g (45%) of desired product (mixture of isomers) as an oil. $^1$H NMR (DMSO-d$_6$): δ 7.32-7.25 (m, 15H), 6.57 (d, J=4.8 Hz, 0.7H, D$_2$O exchangeable), 5.82 (d, J=7.7 Hz, 0.3H), 5.26 (dd, J=7.7, 3.5 Hz, 0.3H), 5.21 (dd, J=4.8, 1.3 Hz, 0.7H), 4.70-4.43 (m, 6H), 4.16 (q, J=4.1 Hz, 0.3H), 4.06-3.96 (m, 1.3H), 3.93-3.87 (m, 0.7H), 3.80 (dd, J=4.3, 1.5 Hz, 0.7H), 3.58-3.41 (m, 2H);

Step 4: To a stirred solution of product from Step 3 (15 g, 35.67 mmol) in THF (150 mL) was added diethyl (cyanomethyl)phosphonate (6.95 g, 39.23 mmol) at room temperature followed by lithium bis(trimethylsilyl)amide (39.2 mL, 1M solution in THF) addition at −78° C. The reaction mixture was stirred at −78° C. for about 20 min and at 0° C. for 1.5 h and then was quenched by adding water (50 mL). The reaction was extracted with ether (2×200 mL), washed with water (2×50 mL), brine (1×50 mL), and dried over Mg SO$_4$. After filtration, the filtrate was concentrated and purified by flash chromatography using 0 to 30% ethyl acetate in hexanes to give 10.79 g (68.2%) of desired compound as a mixture of isomers as an oil. MS (ES$^+$) 444.33 (M+1).

EXAMPLE B-1

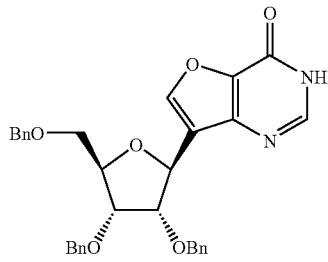

7-β-(2',3',5'-Tri-O-benzyl-D-ribofuranosyl)-furo[3,2-d]pyrimidin-4(3H)-one (Scheme B-1)

Step 1: To a stirred solution of compound from Step 4 of example A-1, (3S,4R,5R)-(3,4-bis-benzyloxy-5-benzyloxymethyl-tetrahydro-furan-2-yl)-acetonitrile (10.7 g, 24.12 mmol) in DMF (150 mL) was added tert-butoxybis(dimethylamino)methane (21.02 g, 120.62 mmol) at room temperature and stirred for 12 h. The reaction mixture was diluted with toluene (700 mL) and washed with water (2×250 mL), brine (1×50 mL) and dried (MgSO$_4$). After filtration, the filtrate was concentrated to give (13.8 g) of desired product, which was used as such for next step.

Step 2: The compound from Step 1 (13.8 g, 24.12 mmol) was dissolved in chloroform (250 mL), trifluoroacetic acid (4.59 g, 40.29 mmol) and water (137 mL) at room temperature and stirred for 18 h. The organic layer was separated and the aqueous layer was extracted with chloroform (2×200 mL). The combined organic extracts were washed with water (2×200 mL), brine (1×100 mL), and dried (MgSO$_4$). After filtration, the filtrate was concentrated to afford 12.59 g of desired product. A small amount was taken out and purified on silica gel column using ethyl acetate and hexanes. MS (ES$^+$) 494.20 (M+23), (ES$^-$) 470.28 (M−1); Anal. Calcd for C$_{29}$H$_{29}$NO$_5$·0.75H$_2$O: C, 71.80; H, 6.33; N, 2.88. Found: C, 71.95; H, 6.04; N, 2.88.

Step 3: To a stirred solution of product from Step 2, (186.5 g, 395.4 mmol) in DMF (1500 mL) was added sodium hydride (19.7 g, 60%, 494.3 mmol) in four portions at 0° C. over a period of 1.5 h followed by 2-bromodiethylmalonate (118.1 g, 494.3 mmol) over a period of 30 min at 0° C. and stirred at room temperature for 12 h. After diluting with water (1000 mL), the reaction mixture was extracted with ethyl acetate (3×2000 mL). The combined organic extracts were washed with water (2×1000 mL), brine (1×200 mL), and dried (MgSO$_4$). After filtration, the filtrate was concentrated to give 296 g of crude desired product, which was used in the next reaction without further purification.

Step 4: To a compound from Step 3 (296 g, crude) in EtOH (1000 mL) was added 1,5-diazabicyclo[4.3.0]non-5-ene (58.9 g, 474.48 mmol) at room temperature and stirred for 18 h. The reaction mixture was concentrated and the residue was dissolved in ethyl acetate (4000 mL), washed with water (2×1000 mL), brine (2×500 mL), and dried (MgSO$_4$). After filtration, the filtrate was concentrated and the crude residue was purified by flash chromatography on silica gel using ethyl acetate and hexanes to afford 29 g, (13.1%) of the desired product as light brown oil.

Step 5: To a stirred solution of compound from Step 4 (29.0 g, 52.04 mmol) in EtOH (600 mL) was added formamidine acetate (135 g, 1301 mmol) at room temperature and heated at reflux for four days and the solid material was removed by filtration and filtrate was concentrated. The residue was dissolved in chloroform (400 mL), washed with water (2×100 mL), brine (1×100 mL), and dried (MgSO$_4$). The crude residue was purified by flash chromatography on silica gel using CMA-80 in chloroform (0 to 20%) to afford 12 g (42.8%) of the desired product (12 g, 42.8%) as a colorless crystalline solid; mp 88-100° C. $^1$H NMR (DMSO-d$_6$): δ 12.66 (bs, 1H, D$_2$O exchangeable), 8.11 (s, 1H), 8.05 (d, J=2.8 Hz, 1H), 7.33-7.25 (m, 15H), 5.11 (d, J=4.8 Hz, 1H), 4.61 (s, 2H), 4.58-4.48 (m, 4H), 4.4 (t, J=4.7 Hz, 1H), 4.19-4.12 (m, 2H), 3.63 (ddd, J=23.3, 10.7. 3.2 Hz, 2H); MS (ES$^+$) 539.43 (M+1), 561.42 (M+23), (ES$^-$) 537.44 (M−1); Anal. Calcd for C$_{32}$H$_{30}$N$_2$O$_6$: C, 71.36; H, 5.61; N, 5.20. Found: C, 71.30; H, 5.54; N, 5.10.

EXAMPLE B-2

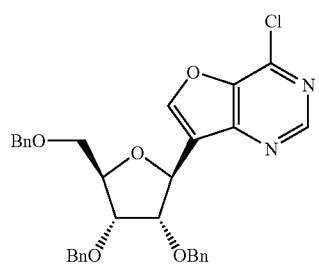

4-Chloro-7-β-(2',3',5'-tri-O-benzyl-D-ribofuranosyl)-furo[3,2-d]pyrimidine (Scheme B-2)

To a stirred solution of compound from Example B-1, Step 5, (6.26 g, 11.62 mmol), benzyltriethylammonium chloride (5.29 g, 23.24 mmol), N,N-dimethylaniline (2.12 g, 17.43 mmol) in acetonitrile (50 mL) was added phosphorous oxychloride (10.69 g, 69.74 mmol) at 80° C. and further stirred at 80° C. for 30 min. Then the reaction was concentrated to dryness, dissolved in chloroform (100 mL) and quenched with water (50 mL). The organic layer was separated and aqueous layer was further extracted with chloroform (2×50 mL). The combined chloroform extracts were washed with water (2×100 mL), sat. NaHCO$_3$ (1×50 mL), water (1×100 mL), and brine (1×50 mL), and dried (MgSO$_4$). After filtration, the filtrate was concentrated and the residue was purified by flash chromatography on silica gel column using ethyl acetate in hexanes (0 to 25%) to afford 5.62 g (86.8%) of desired product as a colorless crystalline solid. $^1$H NMR (DMSO-d$_6$): δ 8.87 (s, 1H), 8.54 (s, 1H), 7.33-7.19 (m, 15H), 5.21 (d, J=5.1 Hz, 1H), 4.66-4.47 (m, 7H), 4.24-4.18 (m, 2H), 3.66 (ddd, J=23.1, 10.5. 3.5 Hz, 2H); Anal. Calcd for C$_{32}$H$_{29}$Cl N$_2$O$_5$: C, 68.99; H, 5.24; Cl, 6.36; N, 5.02. Found: C, 69.12; H, 5.19; Cl, 6.30; N, 5.04.

GENERAL METHOD OF PREPARATION OF COMPOUNDS IN EXAMPLES B-3 TO B-19

Step 1: A solution of chloro compound from example B-2 (1 equiv.), appropriate amine (6 equiv.), and triethylamine (20 equiv.) in ethanol was heated at 35 to 45° C. for 5 h to 15 h. After concentration, the residue was partitioned between chloroform or ethyl acetate and water. The organic layer was washed with water and brine, dried over MgSO$_4$. After filtration the residue was purified by crystallization or on silica gel column using appropriate solvent system.

Step 2: A solution of product from step 1 (1 equiv.) in dichloromethane was treated with 1M solution of BCl$_3$ in dichloromethane (2 to 10 equiv.) at 0 to −78° C. and stirred for 1-3 h. The reaction mixture was quenched with methanol and concentrated to dryness. The residue was co-evaporated with HCl and ethanol mixture two times and with ethanol two times. The residue was purified by re-crystallization or silica gel column using appropriate solvent system.

EXAMPLE B-3

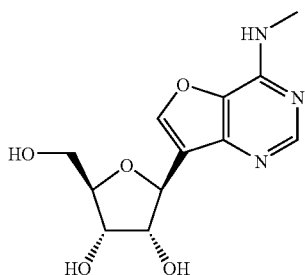

4-Methylamino-7-β-(D-ribofuranosyl)-furo[3,2-d] pyrimidine (Scheme B-3)

$^1$H NMR (DMSO-d$_6$): δ 8.30 (s, 1H), 8.21(s, 1H), 7.93 (d, J=4.7 Hz, 1H, D$_2$O exchangeable), 5.80 (dd, J=9.4, 3.3 Hz, 1H, D$_2$O exchangeable), 5.05 (d, J=6.4 Hz, 1H, D$_2$O exchangeable), 4.88 (d, J=4.3 Hz, 1H), 4.77 (d, J=7.3, Hz, 1H, D$_2$O exchangeable), 4.35-4.29 (m, 1H), 1.04-4.00 (m, 1H), 3.89 (dd, J=5.4, 2.6 Hz, 1H), 3.63 (td, J=12.0, 3.0 Hz, 1H), 3.52-3.44 (m, 1H), 2.97 (d, J=4.5 Hz, 3H); MS (ES$^+$) 282.51 (M+1)

EXAMPLE B-4

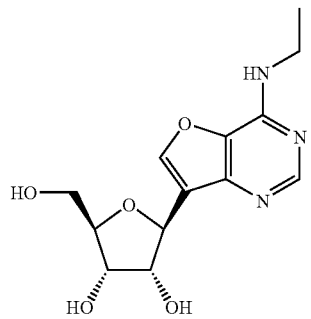

4-Ethylamino-7-β-(D-ribofuranosyl)-furo[3,2-d] pyrimidine (Scheme B-3)

$^1$H NMR (DMSO-d$_6$): δ 8.27 (s, 1H), 8.21 (s, 1H), 8.00 (t, J=5.8 Hz, 1H, D$_2$O exchangeable), 5.81 (d, J=10.1 Hz, 1H, D$_2$O exchangeable), 5.04 (d, J=7.62 Hz, 1H, D$_2$O exchangeable), 4.68 (d, J=6.2 Hz, 1H, D$_2$O exchangeable), 4.76 (d, J=7.3 Hz, 1H), 4.35-4.29 (m, 1H), 4.04-4.00 (m, 1H), 3.89 (dd, J=5.4, 2.8 Hz, 1H), 3.63 (d, J=13.1 Hz, 1H), 3.54-3.46 (m, 3H), 1.18 (t, J=7.15 Hz, 3H); MS (ES$^+$) 296.52 (M+1).

EXAMPLE B-5

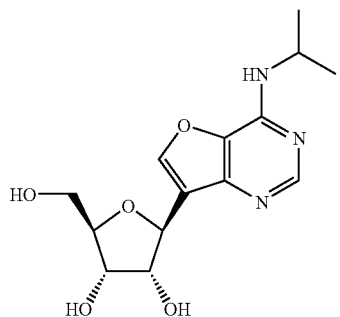

4-Isopropylamino-7-β-(D-ribofuranosyl)-furo[3,2-d] pyrimidine (Scheme B-3)

$^1$H NMR (DMSO-d$_6$): δ 8.27 (s, 1H), 8.21 (s, 1H), 7.84 (d, J=8.1 Hz, 1H, D$_2$O exchangeable), 5.83 (bs, 1H, D$_2$O exchangeable), 5.03 (d, J=6.4 Hz, 1H, D$_2$O exchangeable), 4.88 (d, J=4.3 Hz, 1H, D$_2$O exchangeable), 4.76 (d, J=7.3 Hz, 1H), 4.45-4.29 (m, 2H), 4.04-4.00 (m, 1H), 3.89 (dd, J=5.2, 2.6 Hz, 1H), 3.63 (dd, J=12.0, 2.6 Hz, 1H), 3.53-3.44 (m, 1H), 1.21 (d, J=6.5 Hz, 6H); MS (ES$^-$) 308 (M−1).

EXAMPLE B-6

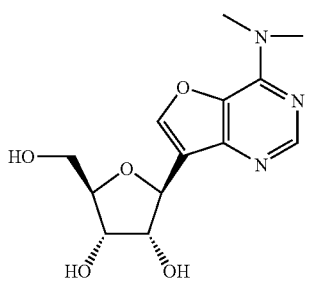

4-Dimethylamino-7-β-(D-ribofuranosyl)-furo[3,2-d]pyrimidine (Scheme B-3)

$^1$H NMR (DMSO-d$_6$): δ 8.29 (s, 1H), 8.24 (s, 1H), 5.76 (dd, J=9.4, 3.4 Hz, 1H, D$_2$O exchangeable), 5.05 (d, J=6.2 Hz, 1H, D$_2$O exchangeable), 4.88 (d, J=4.5 Hz, 1H, D$_2$O exchangeable), 4.78 (d, J=7.3 Hz, 1H), 4.35-4.29 (m, 1H), 4.04-4.00 (m, 1H), 3.89 (dd, J=5.8, 3.0 Hz, 1H), 3.63 (dd, J=12.4, 3.4 Hz, 1H), 3.52-3.44 (m, 1H), 3.33 (s, 6H); MS (ES$^+$) 296.51 (M+1).

EXAMPLE B-7

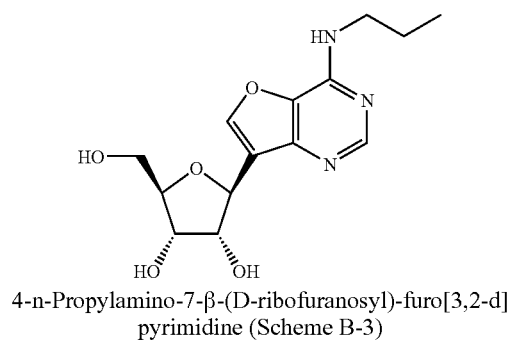

4-n-Propylamino-7-β-(D-ribofuranosyl)-furo[3,2-d]pyrimidine (Scheme B-3)

$^1$H NMR (DMSO-d$_6$): δ 8.27 (s, 1H), 8.21 (s, 1H), 8.03 (bs, 1H, D$_2$O exchangeable), 5.81 (dd, J=9.8, 3.4 Hz, 1H, D$_2$O exchangeable), 5.04 (d, J=6.4 Hz, 1H, D$_2$O exchangeable), 4.88 (d, J=4.3 Hz, 1H, D$_2$O exchangeable), 4.76 (d, J=7.3 Hz, 1H), 4.36-4.29 (m, 1H), 4.04-4.00 (m, 1H), 3.89 (dd, J=5.4, 2.6 Hz, 1H), 3.65-3.60 (m, 1H), 3.52-3.40 (m, 3H), 1.65-1.54 (m, 2H), 0.90 (t, J=7.3 Hz, 3H); MS (ES$^+$) 310 (M+1), (ES$^-$) 308.48 (M−1).

EXAMPLE B-8

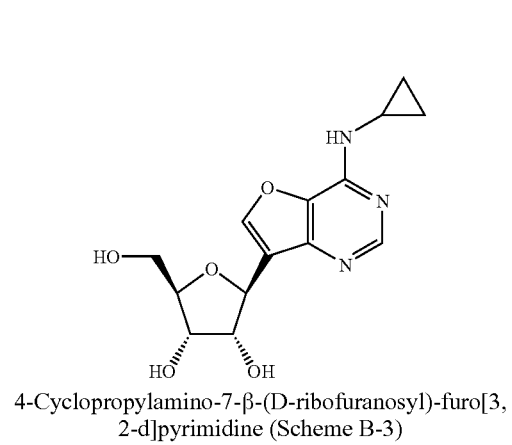

4-Cyclopropylamino-7-β-(D-ribofuranosyl)-furo[3,2-d]pyrimidine (Scheme B-3)

$^1$H NMR (DMSO-d$_6$): δ 8.31 (s, 1H), 8.23 (s, 1H), 8.14 (d, J=3.5 Hz, 1H, D$_2$O exchangeable), 5.77 (dd, J=9.4, 3.4 Hz, 1H, D$_2$O exchangeable), 5.05 (d, J=6.4 Hz, 1H, D$_2$O exchangeable), 4.88 (d, J=4.3 Hz, 1H, D$_2$O exchangeable), 4.77 (d, J=7.3 Hz, 1H), 4.36-4.29 (m, 1H), 4.04-4.00 (m, 1H), 3.89 (dd, J=5.8, 3.2 Hz, 1H), 3.63-3.44 (m, 2H), 3.01-2.92 (m, 1H), 0.79-0.73 (m, 2H), 0.62-0.57 (m, 2H); MS (ES$^+$) 08.52 (M+1), (ES$^-$) 306.46 (M−1).

EXAMPLE B-9

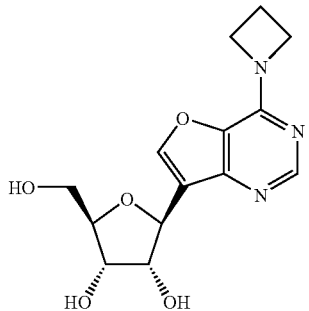

4-Azetidino-7-β-(D-ribofuranosyl)-furo[3,2-d]pyrimidine (Scheme B-3)

$^1$H NMR (DMSO-d$_6$): δ 8.28 (s, 1H), 8.23 (s, 1H), 5.72 (dd, J=9.2, 3.2 Hz, 1H, D$_2$O exchangeable), 5.04 (d, J=6.4 Hz, 1H, D$_2$O exchangeable), 4.88 (d, J=4.5 Hz, 1H, D$_2$O exchangeable), 4.77 (d, J=7.3 Hz, 1H), 4.35-4.28 (m, 5H), 4.03-3.99 (m, 1H), 3.88 (dd, J=5.8, 3.0 Hz, 1H), 3.65-3.44 (m, 2H), 2.49-2.40 (m, 2H); MS (ES$^+$) 308.52 (M+1).

EXAMPLE B-10

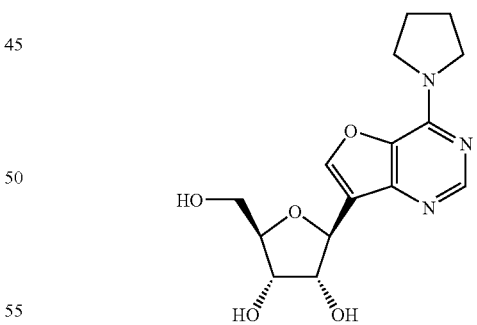

4-Pyrrolidino-7-β-(D-ribofuranosyl)-furo[3,2-d]pyrimidine (Scheme B-3)

$^1$H NMR (DMSO-d$_6$): δ 8.33 (s, 1H), 8.29 (s, 1H), 5.91 (bs, 1H, D$_2$O exchangeable), 5.11 (d, J=6.2 Hz, 1H, D$_2$O exchangeable), 4.95 (d, J=4.3 Hz, 1H, D$_2$O exchangeable), 4.84 (d, J=7.3 Hz, 1H), 4.41-4.35 (m, 1H), 4.10-4.01 (m, 1H), 3.96 (dd, J=5.8, 3.0 Hz, 1H), 3.94-3.67 (m, 5H), 3.58-3.51 (m, 1H), 2.07-1.97 (bs, 4H); MS (ES$^+$) 322.54 (M+1).

EXAMPLE B-11

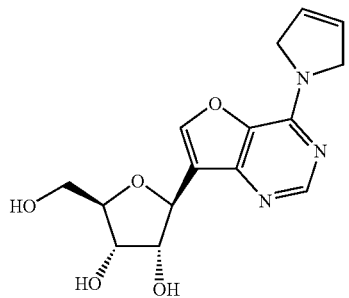

4-(N-3-Pyrrolino)-7-β-(D-ribofuranosyl)-furo[3,2-d]pyrimidine (Scheme B-3)

$^1$HNMR (DMSO-$d_6$): δ 8.74 (s, 1H), 8.54 (s, 1H), 6.10 (br, 2H, olefinic protons), 4.91 (d, J=6.5 Hz, 1H), 4.84 (br, 2H), 4.55 (br, 2H), 4.01-4.10 (m, 2H), 3.88-3.96 (m, 1H), 3.62-3.64 (m, 2H); MS (ES$^+$) 342.33 (M+Na) and (ES$^-$) 318 (M−1).

EXAMPLE B-12

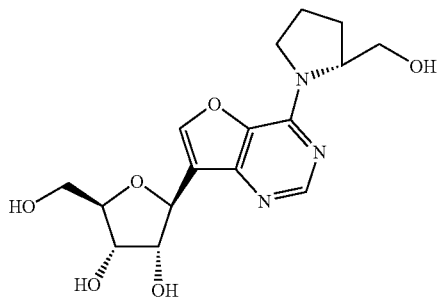

4-(2-Hydroxymethylpyrrolidino)-7-β-(D-ribofuranosyl)-furo[3,2-d]pyrimidine (Scheme B-3)

$^1$HNMR (DMSO-$d_6$): δ 8.72 (s, 1H), 8.55 (s, 1H), 4.91 (d, J=6.0 Hz, 1H), 4.46-4.72 (m, 1H), 3.74-4.10 (m, 5H), 3.42-3.69 (m, 4H), 1.88-2.32 (m, 4H); MS (ES$^+$) 374.34 (M+Na) and (ES$^-$) 350.35 (M−1).

EXAMPLE B-13

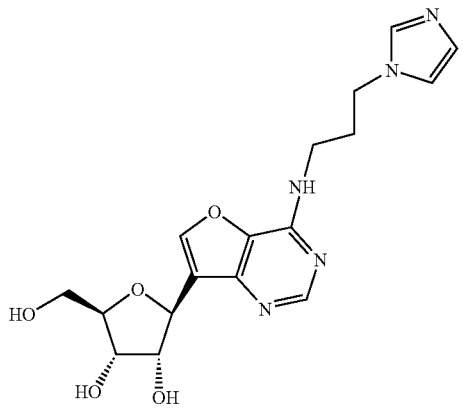

4-(3-N-Imidazolyl-n-propylamino)-7-β-(D-ribofuranosyl)-furo[3,2-d]pyrimidine (Scheme B-3)

$^1$HNMR (DMSO-$d_6$): δ 8.29 (s, 1H), 8.23 (s, 1H), 8.09 (br, 1H), 7.66 (br, 1H), 7.21 (br, 1H), 6.89 (br, 1H), 5.80 (m, 1H), 5.05 (d, J=6.4 Hz, 1H), 4.90 (d, J=4.33 Hz, 1H), 4.77 (d, J=7.34 Hz, 1H), 4.29-4.35 (m, 1H), 4.0 (m, 3H), 3.87-3.90 (m, 1H), 3.60-3.66 (m, 1H), 3.4-3.53 (m, 3H), 1.98-2.03 (m, 2H); MS (ES$^+$) 376.36 (M+1).

EXAMPLE B-14

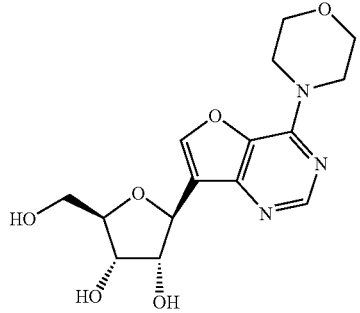

4-N-Morpholino-7-β-(D-ribofuranosyl)-furo[3,2-d]pyrimidine (Scheme B-3)

$^1$HNMR (DMSO-$d_6$): δ 8.71 (s, 1H), 8.53 (s, 1H), 4.91 (d, J=6.5 Hz, 1H), 4.0-4.15 (m, 6H), 3.91-3.94 (m, 1H), 3.76-3.81 (m, 4H), 3.66 (dd, J=12 and 3 Hz 1H), 3.60 (dd, J=12 and 3 Hz, 1H); MS (ES$^+$) 338.38 (M+1) and (ES$^-$) 336.38 (M−1).

EXAMPLE B-15

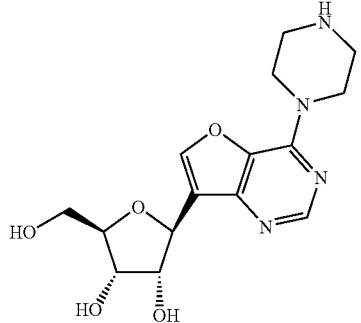

4-N-piperazino-7-β-(D-ribofuranosyl)-furo[3,2-d]pyrimidine (Scheme B-3)

$^1$HNMR (DMSO-$d_6$): δ 8.30 (s, 1H), 8.24 (s, 1H), 5.70 (m, 1H), 5.06 (br, 1H), 4.89 (br, 1H), 4.78 (d, J=7.15 Hz, 1H), 4.28-4.36 (m, 1H), 4.0 (br, 1H), 3.83-3.91 (m, 6H), 3.59-3.67 (m, 1H), 3.4-3.52 (m, 1H), 2.8 (m, 4H); MS (ES$^+$) 337.4 (M+1) and (ES$^-$) 335.38 (M−1).

EXAMPLE B-16

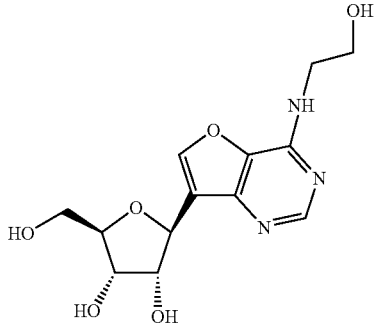

4-(Hydroxyethylamino)-7-β-(D-ribofuranosyl)-furo[3,2-d]pyrimidine (Scheme B-3)

$^1$HNMR (DMSO-$d_6$): δ 8.27 (s, 1H), 8.22 (s, 1H), 7.94 (br, 1H), 5.8 (m, 1H), 5.03 (d, J=6.4 Hz, 1H), 4.89 (d, J=4.14 Hz, 1H), 4.78 (m, 1H), 4.76 (d, J=7.34 Hz, 1H), 4.29-4.36 (m,

1H), 4.0 (m, 1H), 3.8 (m, 1H), 3.4-3.66 (m, 6H); MS (ES⁺) 334.36 (M+Na) and (ES⁻) 310.38 (M−1).

EXAMPLE B-17

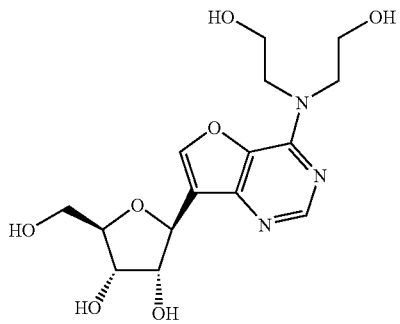

4-(N-Bis-hydroxyethylamino)-7-α-(D-ribofuranosyl)-furo[3,2-d]pyrimidine (Scheme B-3)

¹HNMR (DMSO-d₆): δ 8.27 (s, 1H), 8.22 (s, 1H), 5.78 (m, 1H), 5.04 (d, J=6.21 Hz, 1H), 4.83-4.88 (m, 3H), 4.78 (d, J=7.34 Hz, 1H), 4.3-4.36 (m, 1H), 4.0 (m, 1H), 3.8-3.9 (m, 5H), 3.56-3.69 (m, 5H), 3.44-3.52 (m, 1H); MS (ES⁺) 356.38 (M+1) and (ES⁻) 354.35 (M−1).

EXAMPLE B-18

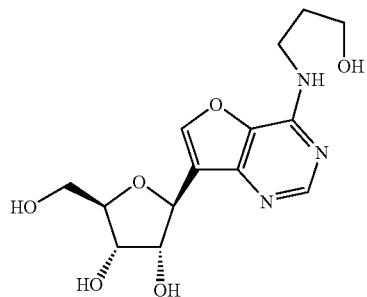

4-(3-Hydroxypropylamino)-7-β-(D-ribofuranosyl)-furo[3,2-d]pyrimidine (Scheme B-3)

¹HNMR (DMSO-d₆): δ 8.27 (s, 1H), 8.21 (s, 1H), 7.97 (br, 1H), 5.80 (m, 1H), 5.04 (d, J=6.4 Hz, 1H), 4.88 (d, J=4.3 Hz, 1H), 4.76 (d, J=7.3 Hz, 1H), 4.52 (t, J=5.08 Hz, 1H), 4.29-4.36 (m, 1H), 4.0 (m, 1H), 3.88-3.90 (m, 1H), 3.60-3.66 (m, 1H), 3.42-3.56 (m, 5H), 1.74 (m, 2H); MS (ES⁺) 326.41 (M+1) and (ES⁻) 324.41 (M−1).

EXAMPLE B-19

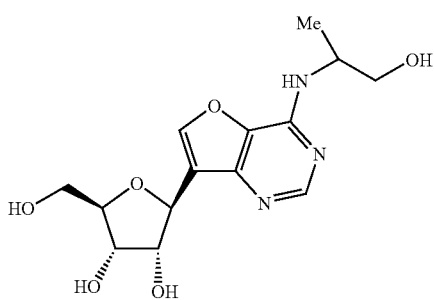

4-(2-Hydroxy-1-methyl-ethylamino)-7-β-(D-ribofuranosyl)-furo[3,2-d]pyrimidine (Scheme B-3)

¹HNMR (DMSO-d₆): δ 8.26 (s, 1H), 8.22 (s, 1H), 7.68 (d, J=8.2 Hz, 1H), 5.80 (m, 1H), 5.04 (dd, J=6.4 and 1.5 Hz, 1H), 4.88 (d, J=4.3 Hz, 1H), 4.78 (m, 1H), 4.76 (d, J=7.3 Hz, 1H), 4.27-4.36 (m, 2H), 4.0 (m, 1H), 3.89 (m, 1. H), 3.58-3.66 (m, 1H), 3.36-3.54 (m, 3H), 1.18 (d, J=6.78 Hz, 3H); MS (ES⁺) 348.37 (M+Na) and (ES⁻) 324.40 (M−1).

EXAMPLE B-20

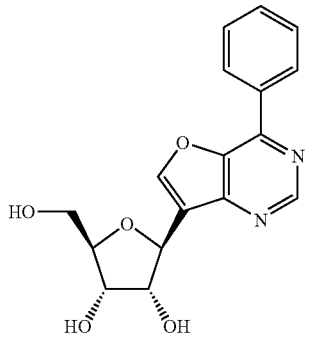

4-Phenyl-7-β-(D-ribofuranosyl)-furo[3,2-d]pyrimidine (Scheme B-3)

Step 1: To a suspension of 10% Pd—C (100 mg) in methanol (50 mL) was added the product from example B-1 (3.0 g, 5.57 mmol) and conc. HCl (0.5 mL) and the mixture was hydrogenated at 70 psi for 16 h. The catalyst was removed by filtration and the filtrate was concentrated to give 7-(3,4-dihydroxy-5-hydroxymethyl-tetrahydro-furan-2-yl)-3H-furo[3,2-d]pyrimidin-4-one (1.66 g), which was used as such for the next step. ¹H NMR (DMSO-d₆): δ 8.24 (s, 1H), 8.12 (s, 1H), 5.03-4.07 (br, 3H, D₂O exchangeable), 4.76 (d, J=6.4 Hz, 1H), 4.23 (dd, J=6.6, 5.1 Hz, 1H), 3.98 (t, J=3.9 Hz, 1H), 3.83 (dd, J=7.3, 3.5 Hz, 1H), 3.60 (dd, J=12.0, 3.5 Hz, 1H), 3.47 (dd, J=12.0, 3.9 Hz, 1H); MS (ES⁺) 269.47 (M+1), MS (ES⁻) 267.43 (M−1).

Step 2: To a stirred solution of the product from step 1 (1.66 g) in pyridine (20 mL) was added benzoyl chloride (5.22 g, 37.16 mmol) at 0° C. and the reaction mixture was brought to RT and stirred for 16 h. After concentration, the residue was dissolved in ethyl acetate (50 mL), washed with water (2×20 mL), brine (1×20 mL), dried (MgSO₄), filtered and the filtrate was concentrated. The crude residue was purified by flash chromatography using ethyl acetate in hexanes (0 to 100%) to give benzoylated product (2.77 g, 77.0%) as a colorless solid. ¹H NMR (DMSO-d₆): δ 12.7 (s, 1H, D₂O exchangeable), 8.39 (s, 1H), 8.04-8.00 (m, 2H), 7.90-7.85 (m, 5H), 7.69-7.61 (m, 3H), 7.54-7.42 (m, 6H), 6.09 (t, J=5.8 Hz, 1H), 5.97 (t, J=5.5 Hz, 1H), 5.47 (d, J=5.6 Hz, 1H), 4.74-4.69 (m, 2H), 4.60 (dd, J=12.9, 5.4 Hz, 1H); MS (ES⁺) 581.37 (M+1), MS (ES⁻) 579.34 (M−1).

Step 3: To a stirred solution of product from step 2 (2.70 g, 4.65 mmol), benzyltriethylammonium chloride (2.07 g, 9.31 mmol), and N,N-dimethylaniline (0.85 g, 6.98 mmol) in acetonitrile (20 mL) was added phosphorous oxychloride (4.28 g, 27.93 mmol) at 80° C. and the mixture was further stirred at 80° C. for 30 min. After concentration, the residue was dissolved in chloroform (100 mL) and washed with water. The organic layer was separated and aqueous layer was further extracted with chloroform (2×30 mL). The combined chloroform extracts were washed with water (2×50 mL), sat. NaHCO₃ (50 mL), water (50 mL), and brine (25 mL), and dried (MgSO₄). After filtration, the filtrate was concentrated and the residue was purified by flash chromatography on silica gel column using ethyl acetate in hexanes (0 to 25%) to afford chloro compound 2.58 g (92.5%) as a colorless crystalline solid. ¹H NMR (DMSO-d₆): δ 8.81 (s, 1H), 8.74 (s, 1H), 8.03-8.01 (m, 2H), 7.92-7.87 (m, 4H), 7.69-7.61 (m, 3H), 7.54-7.42 (m, 6H), 6.15 (t, J=5.8 Hz, 1H), 6.04 (t, J=5.4

Hz, 1H), 5.60 (d, J=5.8 Hz, 1H), 4.80-4.73 (m, 2H), 4.62 (dd, J=12.6, 4.8 Hz, 1H); MS (ES+) 599.36 (M+1), 621.32 (M+Na).

Step 4: To a stirred mixture of chloro compound from step 3 (0.50 g, 0.83 mmol), phenylboronic acid (0.30 g, 2.50 mmol), and sodium bicarbonate (0.32 g, 5.01 mmol) in ethyleneglycol dimethyl ether (10 mL) and water (1 mL) was bubbled nitrogen for 15 min. Dichloro bis triphenylphosphine palladium(II) (58 mg) was added and the mixture was heated to 80° C. for 16 h. The reaction was diluted with water (50 mL) and extracted with ethyl acetate (2×100 mL). The combined organic extracts were washed with water (2×50 mL), brine (25 mL) and dried (MgSO$_4$). After filtration, the filtrate was concentrated and the residue was purified by flash chromatography on silica gel column using ethyl acetate in hexanes (0 to 30%) to afford 449 mg (83.9%) of desired compound as a colorless crystalline solid. $^1$H NMR (DMSO-d$_6$): δ 8.96 (s, 1H), 8.80 (s, 1H), 8.43-8.40 (m, 2H), 8.07-8.04 (m, 2H), 7.93-7.88 (m, 4H), 7.68-7.61 (m, 6H), 7.54-7.42 (m, 6H), 6.26 (t, J=5.8 Hz, 1H), 6.09 (t, J=5.27 Hz, 1H), 5.64 (d, J=5.8 Hz, 1H), 4.81-4.75 (m, 2H), 4.64 (dd, J=12.9, 5.3 Hz, 1H); MS (ES+) 641.43 (M+1).

Step 5: To a stirred solution of product from Step 4 (0.43 g, 0.67 mmol) in methanol (10 mL) was added ammonia saturated in methanol (15 mL) and sealed the reaction mixture in a steel bomb. After stirring for 15 h at RT, the reaction mixture was concentrated to dryness and the residue was purified by flash chromatography on silica gel using CMA-80 in chloroform (0 to 100%) which afforded 110 mg (49.9%) of the desired product as a colorless crystalline solid. $^1$H NMR (DMSO-d$_6$): δ 9.13 (s, 1H), 8.67 (s, 1H), 8.47-8.44 (m, 2H), 7.69-7.63 (m, 3H), 5.14 (d, J=5.8 Hz, 1H, D$_2$O exchangeable), 5.09 (dd, J=7.3, 4.5 Hz, 1H, D$_2$O exchangeable), 4.97 (d, J=5.1 Hz, 1H, D$_2$O exchangeable), 4.94 (d, J=6.4 Hz, 1H), 4.39 (dd, J=10.9, 6.02 Hz, 1H), 4.06 (dd, J=9.2, 4.7 Hz, 1H), 3.89 (dd, J=8.1, 4.1 Hz, 1H), 3.71-3.64 (m, 1H), 3.57-3.49 (m, 1H); MS (ES+) 329.43 (M+1), 351.41 (M+Na), MS (ES−) 327.41 (M−1), 363.35 (M+Cl).

EXAMPLE B-21

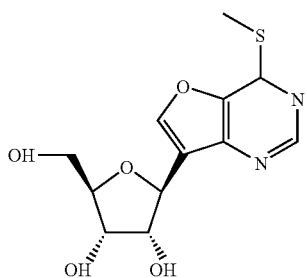

4-Methylthio-7-β-(D-ribofuranosyl)-furo[3,2-d]pyrimidine (Scheme B-3)

The stirred mixture of, 2-(4-chloro-furo[3,2-d]pyrimidin-7-yl)-5-benzoyloxymethyl-tetrahydro-furan-3,4-dibenzoate, product from step-3 of example B-20 (0.35 g, 0.585 mmol) in tetrahydrofuran (15 mL) was treated with sodium thiomethoxide (0.41 g, 5.85 mmol) at RT. After stirring for 16 h at RT, the reaction mixture was concentrated to dryness and the residue was purified on a column of silica gel to afford 0.12 g (68.7%) of the desired product, as a colorless crystalline solid. $^1$HNMR (DMSO-d$_6$): δ 8.87 (s, 1H), 8.47 (s, 1H), 5.12-5.07 (m, 2H, 1H, D$_2$O exchangeable), 4.95 (d, J=5.1 Hz, 1H, D$_2$O exchangeable), 4.86 (d, J=6.6 Hz, 1H, D$_2$O exchangeable), 4.31 (dd, J=11.1, 6.2 Hz, 1H), 4.03 (dd, J=9.4, 4.8 Hz, 1H), 3.87 (q, J=3.7 Hz, 1H), 3.68-3.61 (m, 1H), 3.54-3.46 (m, 1H); MS (ES+): 299.40 (M+1), 321.35 (M+Na), (ES−) 297.38 (M−1).

EXAMPLE B-22

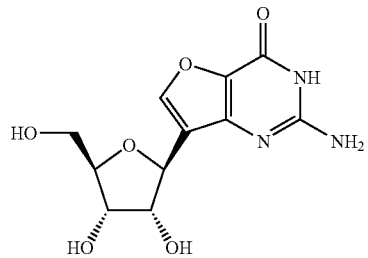

2-Amino-7-β-(D-ribofuranosyl)-furo[3,2-d]pyrimidin-4(3H)-one (Scheme B-4)

Step 1: To a solution of product from step 4 of example B-1 (0.49 g, 0.88 mmol) in pyridine (10 mL) was added triethylamine (0.62 mL, 4.4 mmol), mercury (II) chloride (0.48 g, 1.76 mmol), 1,3 dicarbomethoxy-2-methyl-2-thiopsuedourea (0.37 g, 1.76 mmol) and the reaction mixture was stirred at 50° C. overnight. Reaction was not complete so the same amounts of the reagents were added again and heated at 50° C. for 48 h. Solvent was removed under vacuum and the residue was triturated with ethyl acetate (100 mL) and filtered through a pad of Celite to remove insoluble impurities. The filtrate was concentrated under vacuum and the residue obtained was purified by column chromatography (silica gel 40 g, eluting with 0-75% ethyl acetate in hexanes) to furnish the desired product as yellow oil. It was used as such for the next step Step 2: To a solution of product from Step 1 (0.2 g, 0.28 mmol) in methanol (3 mL) was added sodium methoxide (5.4M solution in methanol, 0.052 mL) and stirred at room temperature overnight. The reaction was quenched with glacial acetic acid (0.04 mL, 1.5 mmol) and concentrated under vacuum to dryness. The residue obtained was purified by column chromatography (silica gel 10 g, eluting with 0-25% CMA-80 in chloroform) to furnish 63 mg (37%) of desired product, 2-methoxycarbonylamino-7-(3,4-bis-benzyloxy-5-benzyloxymethyl-tetrahydrofuran-2-yl)-3H-furo[3,2-d]pyrimidin-4-one, as yellow oil.

Step 3: To the product from Step 2 (60 mg, 0.1 mmol) in methanol (1.0 mL) was added 1N NaOH (0.25 mL, 0.25 mmol) and heated at RT overnight. Again 1N NaOH (0.75 mL) was added and heated at 50° C. for 4 h. The reaction mixture was cooled to room temperature and pH adjusted to 6 using glacial acetic acid. The reaction mixture was concentrated under vacuum to remove methanol and the residue was purified on a column of silica gel to give 41 mg of desired product.

Step 4: A mixture of the product from step 3 (40 mg), 10% Pd/C (40 mg) in methanol (2 mL) and 1N HCl (0.7 mL) was hydrogenated at 50 psi for 6 h. The catalyst was removed by filtration through Celite and the residue was dried to give 25 mg of the product. $^1$H NMR (DMSO-d$_6$): δ 8.11 (s, 1H), 4.69 (d, J=6.9 Hz, 1H), 4.05-4.01 (m, 1H), 3.97-3.95 (m, 1H), 3.89-3.86 (m, 1H), 3.80-3.63 (m, 2H); MS (ES−) 282.34 (M−1).

EXAMPLE C-1

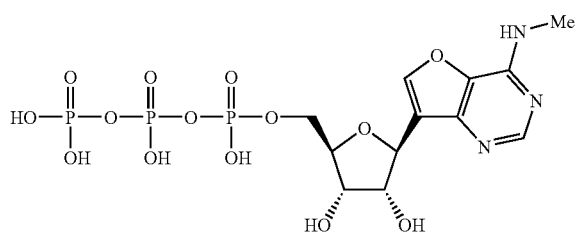

Triphosphate of 4-methylamino-7-β-(D-ribofuranosyl)-furo[3,2-d]pyrimidine

Step 1: A mixture of compound from example B-3 (66 mg, 0.23 mmol), MMTrCl (87 mg, 98%, 0.28 mmol), DMAP (5 mg, 0.04 mmol), and pyridine (2.25 mL) in DMF (1.5 mL) was stirred at room temperature for 22 h. Additional three portions of MMTrCl (87 mg, 180 mg, 180 mg) were added and the reaction mixture was stirred for 15 h, 23 h, and 45 h, respectively after each addition of MMTrCl. The reaction mixture was then treated with triethylamine (1.7 mL, 12.2 mmol), DMAP (14 mg, 0.11 mmol), and 4-nitrobenzoyl chloride (0.87 g, 98%, 4.59 mmol) and stirred at room temperature for 67 h followed by dilution with ethyl acetate (100 mL). Afer washing with water (2×50 mL) and brine (50 mL), the organic phase was dried over $MgSO_4$, fltered and the filtrate was concentrated. The residue was purified on a silica gel column using hexanes/EtOAc (1:0 to 1:1) as eluent to give crude product (269 mg), which was use as such for the next step.

Step 2: A solution of the above product from step 1 (260 mg) in acetonitrile (8 mL) was treated with 0.2 N HCl (0.4 mL) and stired at room temperature for 3 h. The reaction mixture was brought to pH 5 with 0.5 N aq. NaOH followed by dilution with water (20 mL) and concentration to remove most of acetonitrile. The aqueous mixture was extracted with EtOAc (2×25 mL) and chloroform (2×50 mL). The combined extracts were dried over $MgSO_4$. After filtration and concentration, the residue was purified twice on a silica gel column using hexanes/EtOAc/MeOH (1:0:0 to 1:1:0.1) as eluent to give product (47 mg, ~90% pure) which was used as such for next step. MS (ES⁻): 727.65 (M−1).

Step 3: A suspension of the above product from step 2 (45 mg) in a mixture of pyridine (70 μL) and 1,4-dioxane (210 μL) was treated with a freshly prepared solution of chloro-4H-1,3,2-benzodioxaphosphorin-4-one (1M in 1,4-dioxane, 75 μL). The reaction mixture was stirred at room temperature for 20 min followed by treatment with a solution of tributylammonium pyrophosphate, 1.6 $Bu_3N.1.0H_4P_2O_7$ (47 mg, 0.10 mmol) in DMF (205 μL) and tri-n-butylamine (65 μL), simultaneously. The clear solution formed was stirred at room temperature for 30 min followed by treatment with 2.6 mL of 1% $I_2$ in Py/$H_2O$ (98/2). Excess iodine was reduced by 5% aqueous sodium thiosulphate (215 μL) and the resulting solution was concentrated to dryness. The residue was treated with conc. $NH_4OH$ (20 mL). The reaction mixture was stirred at room temperature overnight followed by concentration to dryness. The residue was dissolved in $H_2O$ (20 mL) and washed with $CH_2Cl_2$ (2×15 mL). The aqueous phase was concentrated under vacuum for a short period of time to remove the trace amounts of $CH_2Cl_2$ and purified by DEAE ion exchange column chromatography with a linear gradient of TEAB buffer (1M TEAB buffer, pH=8.0/$H_2O$, 250 mL/250 mL, 0:1 to 1:0). The fractions containing the desired nucleotide were combined and concentrated. The residue was redissolved in $H_2O$ and purified further by HPLC ($CH_3CN$/ 0.1 M TEAB buffer, pH=8.0, 0-20 min, 0-35% $CH_3CN$; 20-28 min, 35-100% $CH_3CN$, monitoring at 260 nm) to give desired triphosphate ($t_R$=15.3 min). $^1$H NMR ($D_2O$): δ 8.17 (s, 1H), 8.04 (s, 1H), 5.00 (d, J=6.0 Hz, 1H), 4.40-4.00 (m, 5H), 2.94 (s, 3H); $^{31}$P NMR ($D_2O$): δ −6.28 (1P), −9.70 (1P), −20.47 (1P); MS (ES⁻): 520.14 (M−1).

EXAMPLE D-1

The following illustrate representative pharmaceutical dosage forms, containing a compound of formula I, or a pharmaceutically acceptable salt or prodrug thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:
1. A compound of the formula:

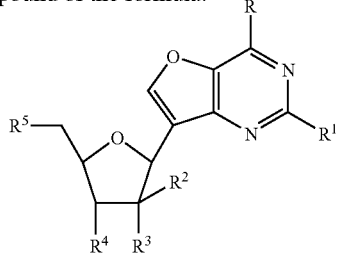

wherein:
R is $NR_eR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n-CH(NHR_a)CO_2R_b$, $(CH_2)_n-S$-alkyl, $(CH_2)_n-S$-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, $CH=N-OR_a$, $NR_aC(=NH)NR_bR_c$, $NR_aC(O)NR_bNR_cR_d$, $O-C(O)R_a$, $OC(O)-OR_a$, $ONH-C(O)O$-alkyl, $ONHC(O)O$-aryl, $ONR_aR_b$, $SNR_aR_b$, $S-ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, and $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

or a pharmaceutically acceptable salt or prodrug thereof.

2. The compound of claim 1 wherein R is, —Cl, $—NR_eR_f$, aryl or $NR_aNR_bR_c$.

3. A compound of the formula:

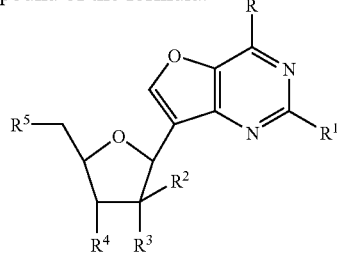

wherein:
R is chloro, methoxy, methylamino, isopropylamino, propylamino, ethylamino, dimethylamino, cyclopropylamino, 2-aminoethylamino, 1-(2-hydroxyethyl)hydrazino, hydrazino, 1-methylhydrazino, azetidino, pyrrolidino, imidazolyipropylamino, pyrrolino, morpholino, piperazino, hydroxyethylamino, bis-hydroxyethylamino, hydroxypropylamino, hydroxyethylpyrrolidino, or 1-methyl-2-hydroxyethylamino;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, N₃, carboxyl, carboxyl esters, thiol, thioalkyl, thioaryl, thioheteroaryl, thiocycloalkyl, thioheterocyclic, cycloalkyl, heteroaryl, and heterocyclic;

or a pharmaceutically acceptable salt or prodrug thereof.

4. A compound of the formula:

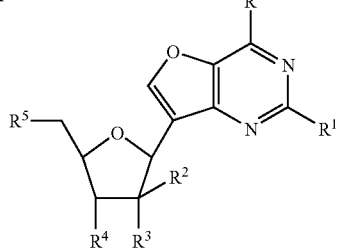

wherein:

R is $NR_eR_f$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, N₃, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, N₃, carboxyl, carboxyl esters, thiol, thioalkyl, thioaryl, thioheteroaryl, thiocycloalkyl, thioheterocyclic, cycloalkyl, heteroaryl, and heterocyclic;

or a pharmaceutically acceptable salt or prodrug thereof.

5. The compound 4-methylamino-7-β-(D-ribofuranosyl)-furo[3,2-d]pyrimidine; 4-Ethylamino-7-β-(D-ribofuranosyl)-furo[3,2-d]pyrimidine; 4-Isopropylamino-7-β-(D-ribofuranosyl)-furo[3,2-d]pyrimidine; 4-Dimethylamino-7-β-(D-ribofuranosyl)-furo[3,2-d]pyrimidine; 4-n-Propylamino-7-β-(D-ribofuranosyl)-furo[3,2-d]pyrimidine; 4-(N-3-pyrrolino)-7-β-(D-ribofuranosyl)-furo[3,2-d]pyrimidine; 4-(2-hydroxymethylpyrrolidino)-7-β-(D-ribofuranosyl)-furo[3,2-d]pyrimidine; 4-(3-N-imidazolyl-n-propylamino)-7-β-(D-ribofuranosyl)-furo[3,2-d]pyrimidine; 4-N-morpholino-7-β-(D-ribofuranosyl)-furo[3,2-d]pyrimidine; 4-N-piperazino-7-β-(D-ribofuranosyl)-furo[3,2-d]pyrimidine; 4-(hydroxyethylamino)-7-β-(D-ribofuranosyl)-furo[3,2-d]pyrimidine; 4-(N-bis-hydroxyethylamino)-7-β-(D-ribofuranosyl)-furo[3,2-d]pyrimidine; 4-(3-hydroxypropylamino)-7-β-(D-ribofuranosyl)-furo[3,2-d]pyrimidine; or 4-(2-hydroxy-1-methyl-ethylamino)-7-β-(D-ribofuranosyl)-furo[3,2-d]pyrimidine;

or a pharmaceutically acceptable salt or prodrug thereof.

6. A prodrug of a compound of the formula:

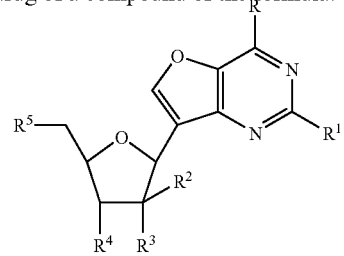

wherein:

R is $OR_a$, $SR_a$, $NR_eR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, $CH=N$—$OR_a$, $NR_aC(=NH)NR_bR_c$, $NR_aC(O)NR_bNR_cR_d$, O—$C(O)R_a$, $OC(O)$—$OR_a$, ONH—$C(O)O$-alkyl, $ONHC(O)O$-aryl, $ONR_aR_b$, $SNR_aR_b$, S—$ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, N₃, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

7. The compound of claim 6 that comprises one or more mono-, di-, or tri-phosphate groups.

8. The compound of claim 7 wherein one or more phosphorous atoms of the one or more pendent mono-, di-, or tri-phosphate groups is bonded to one or more alkoxy or aryloxy groups.

9. The compound of claim 7 wherein one or more phosphorous atoms of the pendent mono-, di-, or tri-phosphate groups is bonded to one or more groups $R_y$—O—; wherein each $R_y$ is independently a 1-20 carbon branched or unbranched, saturated or unsaturated chain, wherein one or more of the carbon atoms is optionally replaced with —O— or —S— and wherein one or more of the carbon atoms is optionally substituted with oxo (=O) or thioxo (=S).

10. The compound of claim 7 wherein one or more phosphorous atoms of the one or more pendent mono-, di-, or tri-phosphate groups is bonded to one or more groups $R_z$—N—; wherein each $R_z$ is a residue of an amino acid.

11. The compound of claim 10 wherein the amino acid is a natural amino acid.

12. The compound of claim 7 which comprises one or more groups of formula:

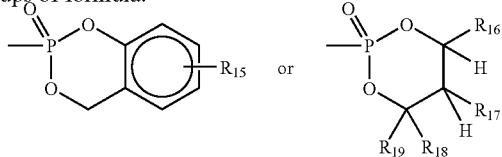

wherein:
$R_{15}$ is H, alkyl, aryl, cycloalkyl, heteroaryl, heterocyclic, or an amino acid;

$R_{16}$ is H, aryl, or heteroaryl; and $R_{17}$ is H, halogen, —CN, —CO—$R_{20}$, —CON($R_{21}$)$_2$, —CO$_2R_{20}$, —SO$_2R_{20}$, —SO$_2$N($R_{21}$)$_2$, —O$R_{21}$, —S$R_{21}$, —$R_{21}$,—N($R_{21}$)$_2$,— O—CO$R_{20}$,—O—CO$_2R_{20}$, —SCO$R_{20}$, —S—CO$_2R_{20}$, —NHCO$R_{21}$,—NHCO$_2R_{21}$,—(CH$_2$)$_p$—OR$_{22}$,or —(CH$_2$)$_p$—SR$_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;

$R_{18}$ and $R_{19}$ are each independently H, alkyl, aryl, aralkyl, aryl, or heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, aralkyl, aryl or heteroaryl;

$R_{20}$ is alkyl, aryl, or arylalkyl;

$R_{21}$ is H, alkyl, aryl, or arylalkyl;

$R_{22}$ is H or lower acyl;

p is an integer from 2-3;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

13. The prodrug of claim 6 wherein one or more of $R^2$, $R^3$, and $R^4$ is acyloxy, acylamino or $R_x$—O; wherein $Rz_x$ is a carboxy-linked amino acid.

14. A pharmaceutical composition comprising a compound as described in claim 1, or a pharmaceutically acceptable salt or prodrug thereof and a pharmaceutically acceptable carrier.

15. A pharmaceutical composition comprising a compound:

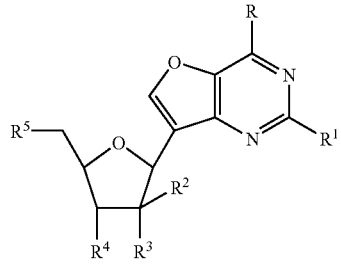

wherein:
R is $OR_a$, $SR_a$, $NR_eR_f$, $NR_aNR_bR_c$, alkyl, alkenyl, alkynyl, aryl, (CH$_2$)$_n$NR$_a$R$_b$, (CH$_2$)$_n$OR$_a$, C(=NR$_a$)NR$_b$R$_c$, (CH$_2$)$_n$—CH(NHR$_a$)CO$_2$R$_b$, (CH$_2$)$_n$—S-alkyl, (CH$_2$)$_n$—S-aryl, Cl, F, Br, I, CN, COOR$_a$, CONR$_a$R$_b$, NHC(=NR$_a$)NHR$_b$, NR$_a$OR$_b$, NR$_a$NO, NHCONHR$_a$, NR$_a$N=NR$_b$, NR$_a$N=CHR$_b$, NR$_a$C(O)NR$_b$R$_c$, NR$_a$C(S)NR$_b$R$_c$, NR$_a$C(O)OR$_b$, CH=N—OR$_a$, NR$_a$C(=NH)NR$_b$R$_c$, NR$_a$C(O)NR$_b$NR$_c$R$_d$, O—C(O)R$_a$, OC(O)—OR$_a$, ONH—C(O)O-alkyl, ONHC(O)O-aryl, ONR$_a$R$_b$, SNR$_a$R$_b$, S—ONR$_a$R$_b$, or SO$_2$NR$_a$R$_b$;

n is 0, 1, 2, 3, 4, or 5;

$R^1$ is H, NR$_a$R$_b$, Cl, F, OR$_a$, SR$_a$, NHCOR$_a$, NHSO$_2$R$_a$, NHCONHR$_a$, CN, alkyl, aryl, ONR$_a$R$_b$, or NR$_a$C(O)OR$_b$;

$R^2$ is H and $R^3$ is OH; or $R^2$ is OH and $R^3$ is H;

$R^4$ is OH, alkyl-O—, alkylC(=O)O, alkyl-S—, or alkylC (=O)—S—;

$R^5$ is OH, alkyl-O—, alkylC(=O)O, alkyl-S—, or alkylC (=O)—S—

$R_a$, $R_b$, $R_c$, $R_d$ are independently selected from the group consisting of H, alkyl, alkenyl, alkynyl, cycloalkyl, heterocyclic, aryl, acyl, SO$_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, SO$_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

or a pharmaceutically acceptable salt or prodrug thereof; and a pharmaceutically acceptable carrier;

which further comprises one or more additional anti-viral agents, immune modulators, or interferon inducers.

16. The composition of claim 15 wherein the one or more anti-viral agents are selected from ribavirin, levovirin, viramidine, thymosin alpha-1, an inhibitor of a serine proteases, an inhibitor of inosine monophosphatedehydrognease, interferon-α, and pegylated interferon-α (peginterferon-α).

17. A pharmaceutical composition comprising a compound:

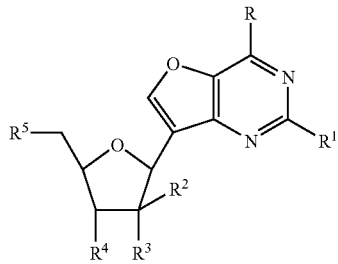

wherein:

$R$ is $OR_a$, $SR_a$, $NR_eR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, $CH=N$—$OR_a$, $NR_aC(=NH)NR_bR_c$, $NR_aC(O)NR_bNR_cR_d$, O—$C(O)R_a$, $OC(O)$—$OR_a$, ONH—C(O)O-alkyl, ONHC(O)O-aryl, $ONR_aR_b$, $SNR_aR_b$, S—$ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

or a pharmaceutically acceptable salt or prodrug thereof; and a pharmacuetically acceptable carrier;

which further comprises one or more additional HCV polymerase inhibitors.

18. A pharmaceutical composition comprising a compound:

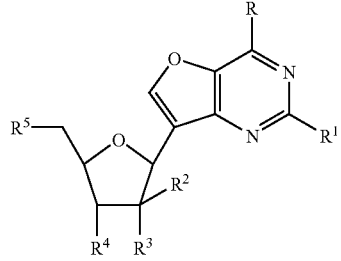

wherein:

$R$ is $OR_a$, $SR_a$, $NR_eR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, $CH=N$—$OR_a$, $NR_aC(=NH)NR_bR_c$, $NR_aC(O)NR_bNR_cR_d$, O—$C(O)R_a$, $OC(O)$—$OR_a$, ONH—C(O)O-alkyl, ONHC(O)O-aryl, $ONR_aR_b$, $SNR_aR_b$, S—$ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

or a pharmaceutically acceptable salt or prodrug thereof; and a pharmacuetically acceptable carrier;

which further comprises one or more protease inhibitors.

19. A pharmaceutical composition comprising a compound:

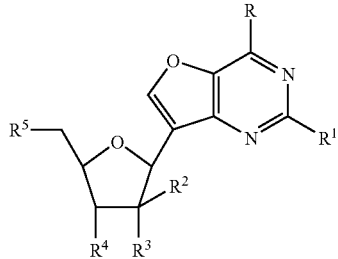

wherein:
R is $OR_a$, $SR_a$, $NR_eR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, CH=N—$OR_a$, $NR_aC(=NH)NR_bR_c$, $NR_aC(O)NR_bNR_cR_d$, O—$C(O)R_a$, OC(O)—$OR_a$, ONH—C(O)O-alkyl, ONHC(O)O-aryl, $ONR_aR_b$, $SNR_aR_b$, S—$ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

or a pharmaceutically acceptable salt or prodrug thereof; and a pharmacuetically acceptable carrier;

which further comprises ribavirin.

20. A pharmaceutical composition comprising a compound:

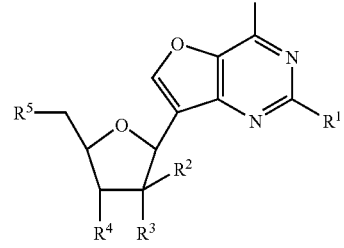

wherein:
R is $OR_a$, $SR_a$, $NR_eR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, CH=N—$OR_a$, $NR_aC(=NH)NR_bR_c$, $NR_aC(O)NR_bNR_cR_d$, O—$C(O)R_a$, OC(O)—$OR_a$, ONH—C(O)O-alkyl, ONHC(O)O-aryl, $ONR_aR_b$, $SNR_aR_b$, S—$ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

or a pharmaceutically acceptable salt or prodrug thereof;

and a pharmacuetically acceptable carrier;

which further comprises interferon-α or pegylated interferon-α (peginterferon-α).

21. A method for treating a viral infection selected from hepatitis B, hepatitis C, Polio, Coxsackie A and B, Rhino, Echo, small pox, Ebola, and West Nile in an animal, comprising administering to the animal an effective amount of a compound that has the formula:

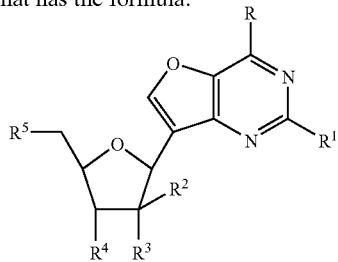

wherein:

R is $OR_a$, $SR_a$, $NR_eR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, CH=N—$OR_a$, $NR_aC(=NH)NR_bR_c$, $NR_aC(O)NR_bNR_cR_d$, O—$C(O)R_a$, OC(O)—$OR_a$, ONH—C(O)O-alkyl, ONHC(O)O-aryl, $ONR_aR_b$, $SNR_aR_b$, S—$ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

or a pharmaceutically acceptable salt or prodrug thereof.

22. The method of claim 21 wherein the viral infection is hepatitis C.

23. The method of claim 21 wherein R is $OR_a$, Cl, $SR_a$, $NR_eR_f$, aryl or $NR_aNR_bR_c$.

24. The method of claim 21 wherein R is hydroxy, chloro, methoxy, mercapto, methylthio, methylamino, isopropylamino, propylamino, ethylamino, dimethylamino, cyclopropylamino, 2-aminoethylamino, 1-(2-hydroxyethyl)hydrazino, hydrazino, 1-methylhydrazino, azetidino, pyrrolidino, imidazolylpropylamino, pyrrolino, morpholino, piperazino, hydroxyethylamino, bis-hydroxyethylamino, hydroxypropylamino, hydroxyethylpyrrolidino, or 1-methyl-2-hydroxyethylamino.

25. The method of claim 21 wherein R is $NR_eR_f$.

26. The method of claim 21 wherein the compound is 4-methylamino-7-β-(D-ribofuranosyl)-furo[3,2-d]pyrimidine; 4-Ethylamino-7-β-(D-ribofuranosyl)-furo[3,2-d]pyrimidine; 4-Isopropylamino-7-β-(D-ribofuranosyl)-furo[3,2-d]pyrimidine; 4-Dimethylamino-7-β-(D-ribofuranosyl)-furo[3,2-d]pyrimidine; 4-n-Propylamino-7-β-(D-ribofuranosyl)-furo[3,2-d]pyrimidine; 4-(N-3-pyrrolino)-7-β-(D-ribofuranosyl)-furo[3,2-d]pyrimidine; 4-(2- hydroxymethylpyrrolidino)-7-β-(D-ribofuranosyl)-furo[3,2-d]pyrimidine; 4-(3-N-imidazolyl-n-propylamino)-7-β-(D-ribofuranosyl)-furo[3,2-d]pyrimidine; 4-N-morpholino-7-α-(D-ribofuranosyl)-furo[3,2-d]pyrimidine; 4-N-piperazino-7-β-(D-ribofuranosyl)-furo[3,2-d]pyrimidine; 4-(hydroxyethylamino)-7-β-(D-ribofuranosyl)-furo[3,2-d]pyrimidine; 4-(N-bis-hydroxyethylamino)-7-β-(D-ribofuranosyl)-furo[3,2-d]pyrimidine; 4-(3-hydroxypropylamino)-7-β-(D-ribofuranosyl)-furo[3,2-d]pyrimidine; or 4-(2-hydroxy-1-methyl-ethylamino)-7-β-(D-ribofuranosyl)-furo[3,2-d]pyrimidine; or a pharmaceutically acceptable salt or prodrug thereof.

27. The method of claim 21 wherein the compound is a prodrug.

28. The method of claim 27 wherein the compound of formula I comprises one or more mono-, di-, or tri-phosphate groups.

29. The method of claim 27 wherein the compound of formula I comprises one or more mono-phosphate groups.

30. The method of claim 28 wherein one or more phosphorous atoms of the one or more pendent mono-, di-, or tri-phosphate groups is bonded to one or more alkoxy or aryloxy groups.

31. The method of claim 28 wherein one or more phosphorous atoms of the pendent mono-, di-, or tri-phosphate groups is bonded to one or more groups $R_y$—O—; wherein each $R_y$ is independently a 1-20 carbon branched or unbranched, saturated or unsaturated chain, wherein one or more of the carbon atoms is optionally replaced with —O— or —S— and wherein one or more of the carbon atoms is optionally substituted with oxo (=O) or thioxo (=S).

32. The method of claim 28 wherein one or more phosphorous atoms of the one or more pendent mono-, di-, or tri-phosphate groups is bonded to one or more groups $R_z$—N—; wherein each $R_z$ is a residue of an amino acid.

33. The method of claim 32 wherein the amino acid is a natural amino acid.

34. The method of claim 28 wherein the compound of formula I comprises one or more groups of formula:

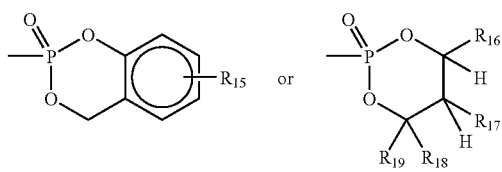

wherein:
$R_{15}$ is H, alkyl, aryl, cycloalkyl, heteroaryl, heterocyclic, or an amino acid;
$R_{16}$ is H, aryl, or heteroaryl; and $R_{17}$ is H, halogen, CN, —CO—$R_{20}$, —CON($R_{21}$)$_2$, —CO$_2R_{20}$, —SO$_2R_{20}$, —SO$_2$N($R_{21}$)$_2$, —OR$_{21}$, —SR$_{21}$, —R$_{21}$, —N($R_{21}$)$_2$, —O—COR$_{20}$, —O—CO$_2R_{20}$, —SCOR$_{20}$, —S—CO$_2R_{20}$, —NHCOR$_{21}$, —NHCO$_2R_{21}$, —(CH$_2$)$_p$—OR$_{22}$, or —(CH$_2$)$_p$—SR$_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;
$R_{18}$ and $R_{19}$ are each independently H, alkyl, aryl, aralkyl, aryl, or heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, aralkyl, aryl or heteroaryl;
$R_{20}$ is alkyl, aryl, or arylalkyl;
$R_{21}$ is H, alkyl, aryl, or arylalkyl;
$R_{22}$ is H or lower acyl;
p is an integer from 2-3;
wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;
and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

35. The method of claim 27 wherein the prodrug is a compound of formula I wherein one or more of $R^2$, $R^3$, and $R^4$ is acyloxy, acylamino or R—O—; wherein R is a carboxy-linked amino acid.

36. The method of claim 21 which further comprises administering to the animal one or more additional viral polymerase inhibitors.

37. The method claim 21 which further comprises administering to the animal, one or more protease inhibitors.

38. The method of claim 21 which further comprises administering ribavirin to the animal.

39. The method of claim 21 which further comprises administering interferon-α or pegylated interferon-α (peginterferon-α) to the animal.

40. The method of claim 21 wherein the virus is hepatitis C.

41. A method for inhibiting an HCV RNA or DNA polymerase comprising contacting the polymerase in vitro or in vivo with an effective inhibitory amount of a compound of the formula:

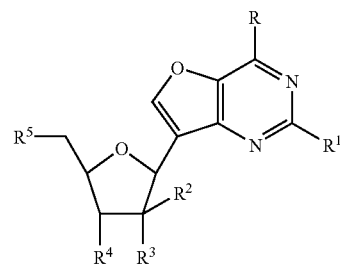

wherein
R is OR$_a$, SR$_a$, NR$_e$R$_f$, NR$_a$NR$_b$R$_c$, alkyl, alkenyl, alkynyl, aryl, (CH$_2$)$_n$NR$_a$R$_b$, (CH$_2$)$_n$OR$_a$, C(=NR$_a$)NR$_b$R$_c$, (CH$_2$)$_n$—CH(NHR$_a$)CO$_2R_b$, (CH$_2$)$_n$—S-alkyl, (CH$_2$)$_n$—S-aryl, Cl, F, Br, I, CN, COOR$_a$, CONR$_a$R$_b$, NHC(=NR$_a$)NHR$_b$, NR$_a$OR$_b$, NR$_a$NO, NHCONHR$_a$, NR$_a$N=NR$_b$, NR$_a$N=CHR$_b$, NR$_a$C(O)NR$_b$R$_c$, NR$_a$C(S)NR$_b$R$_c$, NR$_a$C(O)OR$_b$, CH=N—OR$_a$, NR$_a$C(=NH)NR$_b$R$_c$, NR$_a$C(O)NR$_b$NR$_c$R$_d$, O—C(O)R$_a$, OC(O)—OR$_a$, ONH—C(O)O-alkyl, ONHC(O)O-aryl, ONR$_a$R$_b$, SNR$_a$R$_b$, S—ONR$_a$R$_b$, or SO$_2$NR$_a$R$_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic, or a pharmaceutically acceptable salt or prodrug thereof.

42. A compound of the formula:

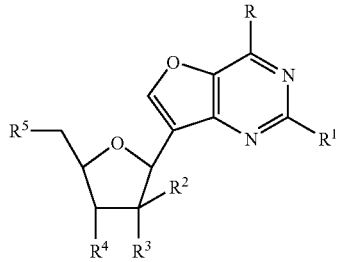

wherein:

R is $OR_a$, $SR_a$, $NR_eR_f$, $NR_aNR_bR_c$, alkyl, alkenyl, alkynyl, aryl, $(CH_2)_nNR_aR_b$, $(CH_2)_nOR_a$, $C(=NR_a)NR_bR_c$, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, CH=N—$OR_a$, $NR_aC(=NH)NR_bR_c$, $NR_aC(O)NR_bNR_aR_d$, O—$C(O)R_a$, OC(O)—$OR_a$, ONH—C(O)O-alkyl, ONHC(O)O-aryl, $ONR_aR_b$, $SNR_aR_b$, S—$ONR_aR_b$, or $SO_2NR_aR_b$;

n is 0, 1, 2, 3, 4, or 5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is H and $R^3$ is OH; or $R^2$ is OH and $R^3$ is H;

$R^4$ is OH, alkyl-O—, alkylC(=O)O, alkyl-S—, or alkylC(=O)—S—;

$R^5$ is OH, alkyl-O—, alkylC(=O)O, alkyl-S—, or alkylC(=O)—S—

$R_a$, $R_b$, $R_c$, $R_d$ are independently selected from the group consisting of H, alkyl, alkenyl, alkynyl, cycloalkyl, heterocyclic, aryl, acyl, $SO_2$-alkyl and NO; or $R_a$ and $R_b$ together with the nitrogen to which they are attached form a pyrrolidino, piperidino, piperazino, azetidino, morpholino, pyrrolino, or thiomorpholino ring; or $R_b$ and $R_c$ together with the nitrogen to which they are attached form a pyrrolidino, piperidino, piperazino, azetidino, morpholino, pyrrolino, or thiomorpholino ring;

$R_e$ is alkyl, alkenyl, alkynyl, cycloalkyl, heterocyclic, aryl, acyl, $SO_2$-alkyl or NO; and $R_f$ is H, alkyl, alkenyl, alkynyl, cycloalkyl, heterocyclic, aryl, acyl, $SO_2$-alkyl and NO; or $R_e$ and $R_f$ together with the nitrogen to which they are attached form a pyrrolidino, piperidino, piperazino, azetidino, morpholino, pyrrolino, or thiomorpholino ring; which ring is optionally substituted with one or more halo, hydroxyl, alkyl, alkenyl, or alkynyl;

wherein any alkyl, cycloalkyl, alkenyl, alkynyl, or acyl is optionally substituted with 1 to 3 substituents selected from the group consisting of alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

and wherein any aryl, heteroaryl, or heterocycle is optionally substituted with 1 to 3 substituents selected from the group consisting of alkyl, alkenyl, alkynyl, alkoxy, acyl, acylamino, acyloxy, oxyacyl, amino, substituted amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic;

or a pharmaceutically acceptable salt or prodrug thereof.

* * * * *